US008716554B2

(12) United States Patent
Michaeli et al.

(10) Patent No.: US 8,716,554 B2
(45) Date of Patent: May 6, 2014

(54) PLANTS RESISTANT TO CYTOPLASM-FEEDING PARASITES

(75) Inventors: Shulamit Michaeli, Kiryat Ono (IL); David Kenigsbuch, Gimzo (IL); Orna Livneh, Rehovot (IL); David Levy, Lapid (IL); Eli Khayat, Western Galilee (IL)

(73) Assignee: Rahan Meristem (1998) Ltd. Plant Propagation & Biotechnology, Kibbutz Rosh Hanikra, Western Galilee (IL)

( * ) Notice: Subject to any disclaimer, the term of this patent is extended or adjusted under 35 U.S.C. 154(b) by 1849 days.

(21) Appl. No.: 10/568,914

(22) PCT Filed: Aug. 22, 2004

(86) PCT No.: PCT/IL2004/000766
§ 371 (c)(1),
(2), (4) Date: Sep. 22, 2006

(87) PCT Pub. No.: WO2005/019408
PCT Pub. Date: Mar. 3, 2005

(65) Prior Publication Data
US 2007/0199100 A1 Aug. 23, 2007

(30) Foreign Application Priority Data
Aug. 21, 2003 (IL) .......................................... 15738

(51) Int. Cl.
C12N 15/01 (2006.01)
C12N 15/82 (2006.01)
C12N 15/87 (2006.01)

(52) U.S. Cl.
USPC ........... 800/279; 800/285; 800/286; 536/24.5

(58) Field of Classification Search
USPC ....................................................... 800/285
See application file for complete search history.

(56) References Cited

U.S. PATENT DOCUMENTS

| 4,407,956 | A | 10/1983 | Howell ...................... 435/91.41 |
| 4,536,475 | A | 8/1985 | Anderson ................... 435/91.1 |
| 4,684,611 | A | 8/1987 | Schilperoort et al. ........ 435/468 |
| 4,940,838 | A | 7/1990 | Schilperoort et al. ........ 800/294 |
| 5,106,739 | A | 4/1992 | Comai et al. ................. 800/294 |
| 5,981,840 | A | 11/1999 | Zhao et al. ................... 800/294 |
| 6,051,757 | A | 4/2000 | Barton et al. ................. 800/294 |
| 6,423,885 | B1 | 7/2002 | Waterhouse et al. ........ 800/278 |
| 6,506,559 | B1 | 1/2003 | Driver et al. ...................... 435/6 |
| 2002/0169298 | A1 | 11/2002 | Waterhouse et al. ........ 536/23.1 |
| 2003/0150017 | A1 | 8/2003 | Mesa et al. .................... 800/279 |
| 2004/0098761 | A1 | 5/2004 | Trick et al. ..................... 800/279 |

FOREIGN PATENT DOCUMENTS

| EP | 0 067 553 | 12/1982 |
| EP | 0 270 356 | 6/1988 |
| WO | WO 84/02913 | 8/1984 |
| WO | WO 85/01856 | 5/1985 |
| WO | WO 89/10396 | 11/1989 |
| WO | WO 92/09696 | 6/1992 |
| WO | WO 92/13956 | 8/1992 |
| WO | WO 98/53083 | 11/1998 |
| WO | WO 99/32619 | 1/1999 |
| WO | WO 99/49029 | 9/1999 |
| WO | WO 99/53050 | 10/1999 |
| WO | WO 00/49035 | 8/2000 |
| WO | WO 01/37654 | * 5/2001 |
| WO | WO 2004/005485 | 1/2004 |

OTHER PUBLICATIONS

Boutla et al., "Short 5'-Phosphorylated Double-Stranded RNAs Induce RNA Interference in *Drosophila*", Curr. Biol. 11(22):1776-1780 (Nov. 2001).
Boutla et al., "Induction of RNA Interference in *Caenorhabditis elegans* by RNAs Derived from Plants Exhibiting Post-transcriptional Gene Silencing", Nucl. Acids Res., 30(7):1688-1694 (2002).
Fire et al., "Potent and Specific Genetic Interference by Double-Stranded RNA in *Caenorhibditis elegans*", Nature, 391:806-811 (Feb. 19, 1998).
Fordham-Skelton et al., "GUS Expression in *Arabidopsis* Directed by 5' Regions of the Pea Metallothionein-like gene PsMT$_4$", Plant Mol. Biol., 34:659-668 (1997).
Holtorf et al., "Comparison of Different Constitutive and Inducible Promoters for the Overexpression of Transgenes in *Arabidopsis thaliana*", Plant Mol. Biol., 29:637-646 (1995).
Kyozuka et al., "Light-Regulated and Cell-Specific Expression of Tomato *rbcS-gusA* and Rice *rbcS-gusA* Fusion Genes in Transgenic Rice", Plant Physiol., 102:991-1000 (1993).
Liu et al., "Isolation of a Novel Collagen Gene (*MJ-COL-5*) in *Meloidogyne javanica* and Analysis of its Expression Pattern", J. Parasitol, 87(4):801-807 (2001).
May et al., "Generation of Transgenic Banana (*Musa acuminata*) Plants via *Agrobacterium*-Mediated Transformation", Bio/Tech, 13:486-492 (May 13, 1995).
Montgomery et al., "Double-Stranded RNA as a Mediator in Sequence-Specific Genetic Silencing and Co-Suppression", TIG, 14(7):255-258 (Jul. 1998).
Morin et al., "Mutations in the *Bemisia tabaci para* Sodium Channel Gene Associated with Resistance to a Pyrethroid Plus Organophosphate Mixture", Insect Biochem. Mol. Biol., 32:1781-1791 (2002).
Wang et al., "A Myb-Related Transcription Factor is Involved in the Phytochrome Regulation of an *Arabidopsis Lhcb* Gene", The Plant Cell, 9:491-507 (Apr. 1997).
International Search Report for PCT/IL2004/000766 dated May 16, 2006.
Written Opinion of the International Searching Authority for PCT/IL2004/000766 dated Oct. 31, 2005.
International Preliminary Report on Patentability for PCT/IL2004/000766 dated Feb. 21, 2006.

(Continued)

Primary Examiner — Li Zheng

(57) ABSTRACT

The present invention relates to transgenic plants resistant to parasites that their normal life cycle includes feeding on the plant cytoplasm, including insects, nematodes and fungi, wherein the plants are engineered to produce small interfering RNAs (siRNAs) capable of silencing a parasite specific gene. Particularly the parasite gene is a stage-specific gene, more particularly a gene involved in essential, early developmental stages of the parasite in or on the plant.

63 Claims, 11 Drawing Sheets

(56) References Cited

OTHER PUBLICATIONS

Basset et al., "Organization and expression of the gene coding for the potassium transport system AKT1 of *Arabidopsis thaliana*", *Plant Mol Biol.*, 29:947-958 (Dec. 1995).

Evans et al, "A gene from pea (*Pisum sativum* L.) with homology to metallothionein genes", *FEBS Lett.*, 262(1):29-32 (Mar. 12, 1990).

Guo et al., "*par-1*, a gene required for establishing polarity in *C. elegans* embryos, encodes a putative Ser/Thr kinase that is asymmetrically distributed", *Cell*, 81:611-620 (May 19, 1995).

Hudspeth et al., "Structure and expression of the maize gene encoding the phosphoenolpyruvate carboxylase isozyme involved in $C_4$ photosynthesis", *Plant Mol Biol*, 12:579-589 (1989).

Hussey et al., "A Comparison of Methods of Collecting Inocula of Meloidogyne SPP., Including a New Technique", *Plant Disease Reporter*, 57(12):1025-1028 (Dec. 1973).

Kagaya et al., "The promoter from the rice nuclear gene encoding chloroplast aldolase confers mesophyll-specific and light-regulated expression in transgenic tobacco", *Mol Gen Genet.*, 248:668-674 (Oct. 25, 1995).

Keller et al., "Specific expression of a novel cell wall hydroxyproline-rich glycoprotein gene in lateral root initiation," *Genes & Dev.*, 3:1639-1646 (Oct. 1989).

Keller et al., "Glycine-rich cell wall proteins in bean: gene structure and association of the protein with the vascular system", *EMBO J.*, 7(12):3625-3633 (Dec. 1, 1988).

Lagarde et al., "Tissue-specific expression of *Arabidopsis AKT1* gene is consistent with a role in $K^+$ nutrition", *Plant J.*, 9(2):195-203 (Feb. 1996).

Linthorst. et al., "Tobacco and tomato PR proteins homologous to win and pro-hevein lack the "hevein" domain", *Mol. Plant Microbe Interact.*, 4(6):586-592 (Nov.-Dec. 1991).

Matton et al., "Cloning, expression, and sequence conservation of pathogenesis-related gene transcripts of potato", *Mol Plant Microbe Interact.*, 2(6):325-331 (Nov.-Dec. 1989).

Mitra et al., "The *Chlorella* virus adenine methyltransferase gene promoter is a strong promoter in plants", *Plant Mol Biol.*, 26:85-93 (Oct. 1994).

Napoli et al., "Introduction of a Chimeric Chalcone Synthase Gene into Petunia Results in Reversible Co-Suppression of Homologous Genes *in trans*", *Plant Cell.*, 2:279-289 (Apr. 1990).

Oppenheimer et al, "The β-tubulin gene family of *Arabidopsis thaliana*: preferential accumulation of the β1 transcript in roots", *Gene*, 63:87-102 (1988).

Peleman et al., "Structure and expression analyses of the S-adenosylmethionine synthetase gene family in *Arabidopsis thaliana*", *Gene*, 84:359-369 (Dec. 14, 1989).

Tabara et al., "RNAi in *C. elegans*: soaking in the genome sequence", *Science*, 282(5388):430-431 (Oct. 16, 1998).

Waterhouse et al., "Molecular cloning and characterisation of asparagine synthetase from *Lotus japonicus*: dynamics of asparagine synthesis in N-sufficient conditions", *Plant Mol. Biol.*, 30:883-897 (Mar. 1996).

Wianny et al., "Specific interference with gene function by double-stranded RNA in early mouse development", *Nat Cell Biol.* 2:70-75 (Feb. 2000).

Xu et al., "Systemic induction of a potato pin2 promoter by wounding, methyl jasmonate, and abscisic acid in transgenic rice plants", *Plant Mol Biol.*, 22(4):573-588 (Jul. 1993).

\* cited by examiner

```
1    gccaaatcct ggccaacttt gaatctgttg atttcaatcg tgggccgaac
51   agttggggcc ttaggaaatt tgacttttgt tttgtgtatc attattttca
101  tttttgctgt gatgggaatg caactattcg ggaagaatta tacagacaat
151  gttgatcgct ttcctggcgg agaactacct cggtggaatt ttactgactt
201  catgcactca ttcatgatcg tttttcgagt cctctgcgga gaatggattg
251  agtccatgtg ggactgtatg catgttggtg atgtgtcctg tattcctttt
301  tttttagcca ctgtcgttat cggttacctt gtagttttaa atctttctt
351  agcgttgttg ctgagtaatt tcggatcatc aagcttatcg gcgccaacag
401  ctgacaacga aacaaacaaa
```

FIGURE 1

```
1    ggaagcacgg gcatgcgaaa gtgcatttgg ttggtcttga tattttctct
51   ggaaagaagt atgaagatat ctgtccatcc actctacaac atggacgttc
101  catttgtaaa gcgtgaagat tatcagttaa cagatatctc cgatgatggc
151  tatctgtgtt tgatgtcaga caatggagat cttcgtgaag acttaaaaat
201  gccagaagga gaattaggtg ttcaactcaa agcagacttc gatagcggag
251  aggagttatt gtgtacagtt ttgaaagctt gtggtgagga gtgtgtaatt
301  gcgatcaaga caaa
```

FIGURE 2

| | | | | |
|---|---|---|---|---|
| 1 | gcgagagggt | ctttccattg | tccttccgtc | cctcgagtac | ctttcacgtt |
| 51 | gttcctccgc | ttaacggcga | tatggaacct | aaagagcagt | tctgccttaa |
| 101 | agagacggta | ttgactaaaa | attttcgaga | aaaatgtatt | tttaaaggat |
| 151 | gagcaccgtc | aaatgcgacg | aattgctttt | attttcgaga | aaaatgtatt |
| 201 | tttaaaggat | gagcaccgtc | aaatgcgacg | aattgctttt | tatagttatg |
| 251 | tacagtcttt | ccaaagccat | ttaattgttg | aaattgacca | ttgtaaggta |
| 301 | aaaaatgaac | ttttgatttt | gttaaacccc | ccttaaattt | tttgaactta |
| 351 | tcttttgcat | tttgatggaa | aaaaagtttt | gtgaccaagc | atgagagatt |
| 401 | atattgagaa | cagccttact | ttattttca | aatgaccttg | aattttaga |
| 451 | attaaatatt | taggcaaaaa | gtcgagatat | gtggctagaa | atgacagcac |
| 501 | ttcaaatcgg | aaaaggacac | gtagaccgag | ttaaacgtgg | ttggctattt |
| 551 | ggccagtggg | tacctgaaaa | tggttacgaa | ccagcacaaa | ctggcccttc |
| 601 | aaatactgtc | caatcagcaa | tatctcaagg | cccaagtggg | gcaacctatg |
| 651 | gacagggagc | tgctggttat | caacctgttg | ttgctccaaa | acccgctcca |
| 701 | gtttgttgta | cttgccatca | aggaccgccc | ggacctatcg | gtcccgaagg |
| 751 | agaacctggg | ccagatgggg | aggatggacc | taatggaaag | gatggaacta |
| 801 | tggaaaaga | tgcacggatt | ttgccagctc | ctttggagcc | tccttgtatt |
| 851 | atatgcccgc | caggacctgc | tggtcctcaa | ggccctgctg | gtgctaaagg |
| 901 | accacctggc | tcgctgggag | agccgccaaa | agacggagtt | cctggtgaac |
| 951 | agggaatggt | tggacaacat | ggtccacccg | gtatgtttgt | ttacaaataa |
| 1001 | atttagactc | ggatgtgtct | gggtctggcg | cggaaactaa | tgtaaatata |
| 1051 | ataattttga | tttcaggacg | acccggacga | gaaggaccta | gaggagcgcc |
| 1101 | tgtcagttta | attaatattt | ctctttaatt | tctttcatat | tcagggctct |
| 1151 | cctggtcgtc | tcattcccgt | gcctggacct | caaggtccag | ctggacctcc |
| 1201 | tggcgttgtt | ggaccaccag | gagcccctgg | agctgccgga | ccacctggtc |
| 1251 | aatcatttga | aggtcctcct | ggacctcctg | gcgagcctgg | acgtcccgga |
| 1301 | cgtgaaggcc | gtcctggcgg | acctgtaagt | ttttatttct | ctaaactttt |
| 1351 | gaagttaatt | tatattttta | acaattcagg | gacctgctgg | acctcctgga |
| 1401 | caagatggag | aaaagggcag | ttgtgaacat | tgtccaggta | tttttcgaaa |
| 1451 | aatattttca | caaattccat | taattttct | ctttttgtg | ttgtatagaa |
| 1501 | ccgcgtactc | ctcccggata | tttcgcggag | gcaagtgcaa | aaagtggtgg |
| 1551 | atatcattaa | ttattattgt | gatattaaac | tactactact | ttttattctt |
| 1601 | tcaaacaaaa | agaaggaacc | agttaggaaa | ttt | |

FIGURE 3

```
1     gagctcctcc ttctcgacta gcctccgcct ccgcctcttc tccgtcgtgc
51    atttcacttc ccacacttcc gattcagtct catacccgtg ccgctaaagc
101   cactgcttac tgttcgtttt ccataaatct gaagattttt cttttcactt
151   ttaatttcga gtttaaagtt tcaaactttc gaaatgggtt ttggttttta
201   ggtcggaaga ttgtgaggaa cgttgtgacg agagctacta ctgaagttgg
251   tgaagctcct gccactacta ccgaagctga gactactgag ttacctgaaa
301   tcgtcaagac tgctcaagaa gctgtaaata ctcttacttt atttatacaa
351   tgatgattct acctcttgct tctgggttac atgtactgaa tttggttgtt
401   tggattgaag tgggagaaag tggatgacaa gacgctattg gttctcttgc
451   ctttgctggt gtagtggctc tttggggttc tgctggaatg atttcggtga
501   gtagaagaat actactttct tcttaaaacc ctagtgttaa atttccttta
551   tttgattcca aaatttgtta ttgtgaaaca ggcaatcgat aggcttccat
601   tggttcctgg tgttcttgaa cttgtaggca tcggttacac aggagtgagt
651   ttcttcttct ctttgtatca cttgaaccaa agctctcatg aacctgtttt
701   gaggatatag atgattcatc acttcacttt tggatttagg attagttctc
751   tgaatttaga atccgaacat ctgcaattca tatggagata tgatatcaga
801   aattgattgc tgcttctcgc tagtgtttca atcttaaaag acgtgtgtag
851   tttgtttcaa ttgtgtgatg gaccttatta acatttggtt tttctatggc
901   agtggttcac ttacaagaac ctggtcttca aaccagacag gttaaccaat
951   tctctcttta actctgtgtt tggttgcatg taatactgag aatggaagac
1001  tcaaattctc gaggaaattg tttgttatct gtttcaggga ggctttgttt
1051  gagaaggtca agagcacata caaagacata ttagggagca gctgaatcaa
1101  aggaggaaga agaagaagaa gagcctttt gaggccattc atgaattgga
1151  atgaaggata tcaaaagaat ctaacacaaa ggccacgtcc ttccttcaat
1201  ctttccttct tgtaactaaa taattttcat cctttctctc tctctgtctc
1251  tggtcttttt tagctcaaag tatcatccat ttatgtcaaa gtgttgtaaa
1301  ttcctcaaga ctatatatga gatgttttgt ttcatttttcc aaaatttcaa
1351  actttgtccc catttagtct tctacccttc atgcatggtt agcttagctt
1401  aatgctgaac tgttgaataa cgatatgggc cttatgctaa agaacaaaa
1451  ccttatgggt ctaaaaaaaa taagcccaat ataaaactat ggcccaaata
1501  agtttaggtc cattagagtg tgagaatagc gcgtgtagtg aaccgcacga
1551  gaatgcgcgt tcgattgttg gtgaagtagt cgtctagatt cccgggtcca
```

FIGURE 4

```
1601    ctgatgtttc tagtgtatca gacacgtgtc gacaaactgg tgggagagat
1651    taacgatctt aagtaggtcc cactagatca agatattata acgaattgac
1701    cttttaacc tttcaggtag tcccggaact cgtggcctag aatacaaaga
1751    aggttgtgaa caagttgatg ttaagatgga caagaatgta acttgaacaa
1801    aagctgaatc atctcttcag ccactagtat gttgacatat ggcagtttct
1851    tttgtagcct cgaaataaat aaattaaaaa gtttgaggtt aaagataatt
1901    atagtggctg agatttctcc atttccgtag cttctggtct cttttctttg
1951    tttcattgat caaaagcaaa tcacttcttc ttcttcttct tctcgatttc
2001    ttactgtttt cttatccaac gaaatctgga attaaaatg gaatctttat
2051    cgaatccaag ctgattttgt ttctttcatt gaatcatctc tctaaaggta
2101    cttaagattg atttattgtc atggtctttc ttattgtttg atgaataact
2151    tgacttgatt gttttttgtt ttgtggatta gtggaatttt gtaaagagaa
2201    gatctgaagt tgtgtagagg agcttagtga tggagacaaa ttcgtctgga
2251    gaagatctgg ttattaaggt aaattaacta aattttaggg ggaagatgat
2301    tgttttaggt gtcaaagatt gagaatttta atgaaacttg atatagactc
2351    ggaagccata tacgataaca aagcaacgtg aaaggtggac tgaggaagaa
2401    cataatagat tcattgaagc tttgaggctt tatggtagag catggcagaa
2451    gattgaaggt tgattttat ttccctttat atgtcttatt ttttgtgttt
2501    gcagaggttt gtcttcaaac tgatttgctt ttttcattt ggacagaaca
2551    tgtagcaaca aaaactgctg tccagataag aagtcacgct cagaaatttt
2601    tctccaaggt aaaatcggtt aattttgaaa tgatgttctc atcttcattg
2651    gcttaatgct taagacttat tgaaagccag gcaagttttc tgcttctttt
2701    gcttcttagt caggagatag atagattacg tttttagagt ttagtaatga
2751    gcaataagtc ttaaaatagt tggagaaatg acgagatgta atcgttttct
2801    tttgtttatg cctatatctt gttaatccac aaacatgtac atagattctt
2851    cagaagaatg ttagtttctt tagattcttc agataaactt gtgtcttctt
2901    accgattctg aggtagtggc aaaagtgggc tgagtgctag aaatttttga
2951    atgttccttg tgataagcca tagaggtaaa ccatttttga ttttccagtt
3001    ctgtcattta aacttgttag gtgtcattag attttgttt gtttacgttt
3051    gtttagaggg taacaaaact actctcatct ctctcaggta gagaaagagg
3101    ctgaagctaa aggtgtagct atgggtcaag cgctagacat agctattcct
3151    cctccacggc ctaagcgtaa accaaacaat ccttatcctc gaaagacggg
```

FIGURE 4 CONT.

3201 aagtggaacg atccttatgt caaaaacggg tgtgaatgat ggaaaagagt
3251 cccttggatc agaaaaagtg tcgcatcctg aggtgatttt catggtcata
3301 tggcatcttt ttgcagtgtg tcacattgct cctcatgtta ttaatacaga
3351 ttgtgtgctt cgtttataga tggccaatga agatcgacaa caatcaaagc
3401 ctgaagagaa aactctgcag gaagacaact gttcagattg tttcactcat
3451 cagtatctct ctgctgcatc ctccatgaat aaaagttgta tagagacatc
3501 aaacgcaagc actttccgcg agttcttgcc ttcacgggaa gaggtaaaaa
3551 acaatctttc attgctattt gaggttttaa gacgattagt acttttcatg
3601 aaactaaaac cgtgggggaa taacagggaa gtcagaataa cagggtaaga
3651 aaggagtcaa actcagattt gaatgcaaaa tctctggaaa acggtaatga
3701 gcaaggacct cagacttatc cgatgcatat ccctgtgcta gtgccattgg
3751 ggagctcaat aacaagttct ctatcacatc ctccttcaga gccagatagt
3801 catccccaca cagttgcagg agattatcag tcgtttccta atcatataat
3851 gtcaacccct ttacaaacac cggctcttta tactgccgca actttcgcct
3901 catcattttg gcctcccgat tctagtggtg gctcacctgt tccagggaac
3951 tcacctccga atctggctgc catggccgca gccactgttg cagctgctag
4001 tgcttggtgg gctgccaatg gattattacc tttatgtgct cctcttagtt
4051 caggtggttt cactagtcat cctccatcta cttttggacc atcatgtgat
4101 gtagagtaca caaaagcaag cactttacaa catggttctg tgcagagccg
4151 agagcaagaa cactccgagg catcaaaggc tcgatcttca ctggactcag
4201 aggatgttga aaataagagt aaaccagttt gtcatgagca gccttctgca
4251 acacctgaga gtgatgcaaa gggttcagat ggagcaggag acagaaaaca
4301 agttgaccgg tcctcgtgtg gctcaaacac tccgtcgagt agtgatgatg
4351 ttgaggcgga tgcatcagaa aggcaagagg atggcaccaa tggtgaggtg
4401 aaagaaacga atgaagacac taataaacct caaacttcag agtccaatgc
4451 acgccgcagt agaatcagct ccaatataac cgatccatgg aagtctgtgt
4501 ctgacgaggt acttacttgg actaaagatc aacttccttt atttcaaatc
4551 attttctcat ataaatattg tacattcggg tcgaattgcc ttccaagctc
4601 tcttctccag agaggtattg ccgcaaagtt ttacatatcg agaagaacac

FIGURE 4 CONT.

```
4651  agagaggaag aacaacaaca acaagaacaa agatatccaa tggcacttga
4701  tcttaacttc acagctcagt taacaccagt tgatgatcaa gaggagaaga
4751  gaaacacagg atttcttgga atcggattag atgcttcaaa gctaatgagt
4801  agaggaagaa caggttttaa accatacaaa agatgttcca tggaagccaa
4851  agaaagtaga atcctcaaca acaatcctat cattcatgtg aacagaaag
4901  atcccaaacg gatgcggttg gaaactcaag cttccacatg agactctatt
4951  ttcatctgat ctgttgtttg tactctgttt ttaagttttc aagaccactg
5001  ctacattttc ttttctttt gaggcctttg tatttgtttc cttgtccata
5051  gtcttcctgt aacatttgac tctgtattat tcaacaaatc ataaactgtt
5101  taatctttt ttttccaacc tggaaagaac ttcactcaag gggctcttgt
5151  tcttgatata tgcaaacgac agagttccaa aacgtaatct tagcccatcc
5201  atcaccctta agttgtctca taactcataa gtaagcacaa aa
```

FIGURE 4 CONT.

```
B. tabaci:     MADVEAHFETGDSGASTTYPMQCSALRKNGFVMLKARPCKIVDMSTSKTGKHGHA
               MAD++ HFET DSGAS+TYPMQCSALRKNGFVMLK+RPCKIV+MSTSKTGKHGHA
D. yakuba: 1   MADMDDHFETTDSGASSTYPMQCSALRKNGFVMLKSRPCKIVEMSTSKTGKHGHA 55
```

PLANTS RESISTANT TO CYTOPLASM-FEEDING PARASITES

RELATED APPLICATION DATA

This application is the U.S. national stage of PCT/IL2004/000766 filed on Aug. 22, 2004, which is based on and claims the benefit of Israeli Patent Application No. 157538 filed on Aug. 21, 2003, which is incorporated herein in its entirety by this reference.

FIELD OF THE INVENTION

The present invention relates to transgenic plants resistant to parasites that feed on the plant cytoplasm, including cytoplasm-feeding insects, nematodes and fungi, wherein the plants are engineered to produce small interfering RNAs (siRNAs) capable of silencing a parasite specific gene, particularly a stage-specific gene, more particularly a gene involved in early developmental stages.

BACKGROUND OF THE INVENTION

Parasites feeding on plants affect a variety of crops, especially those cultivated in tropical and Mediterranean climates, presenting a major agricultural problem causing damage estimated in the range of billions of dollars. Such parasites include parasites whose life cycle comprises at least one stage of consumption of plant cytoplasm, including insects, nematodes, and fungi. One approach for reducing such parasite damage is by generating resistant plants, either by genetic selection of natural resistant varieties or by introducing genetic resistance artificially.

Inhibitory RNA (RNAi) has become an important tool for silencing genes in many eukaryotes. It was discovered in the nematode *Caenorhabditis elegans* (Guo, S. and Kemphues, K. J. 1995. Cell 81:611-620) and was later shown to exist in *Trypanosoma brucei, Drosophila, Neurospora* and more recently in plants and mammalian cells (Wianny, F. and Zernicka-Goetz, M., 2000. Nat. Cell Biol. 2:70-75). In plants, post-transcriptional gene silencing (PTGS), known as co-suppression is mechanistically related to RNAi (see for example, Napoli, C. Lemiex C and Jorgensen R. 1990. Plant Cell 2:279-289). In *C. elegans* the phenomenon was demonstrated to be triggered by administration of dsRNA to the whole organism (Tabara, H. Grishok A. and Mello C. C. 1998. Science 282:430-431).

WO 98/53083 describes constructs and methods for enhancing the inhibition of a target gene within an organism, which involve inserting into a gene-silencing vector an inverted repeat sequence for all or part of a polynucleotide region within the vector. The inverted repeat sequence may be a synthetic polynucleotide sequence or comprise a modified natural polynucleotide sequence.

WO 99/32619 discloses a process of introducing RNA into a living cell to inhibit gene expression of a target gene in that cell. The RNA has a region with a double-stranded structure. Inhibition is sequence-specific in that the nucleotide sequence of the duplex region of the RNA and of a portion of the target gene are identical.

WO 99/49029 relates to a method of modifying gene expression and to synthetic genes for modifying endogenous gene expression in a cell, tissue or organ of a transgenic organism, in particular a transgenic animal or plant. Recombinant DNA technology is used to post-transcriptionally modify or modulate the expression of a target gene in a cell, tissue, or organ, by introducing multiple copies of a nucleotide sequence which is substantially identical to the nucleic acid sequence of the target gene or to the complementary sequence of the target gene under conditions sufficient for translation of the mRNA of the target gene to be modified.

WO 99/53050 discloses methods and means for reducing the phenotypic expression of a nucleic acid of interest in eukaryotic cells, particularly in plant cells, by introducing chimeric genes encoding sense and antisense RNA molecules directed towards the target nucleic acid, which are capable of forming a double stranded RNA region by base-pairing between the regions with sense and antisense nucleotide sequence or, alternatively, by introducing the RNA molecules themselves. Preferably, the RNA molecules comprise simultaneously both sense and antisense nucleotide sequences. Specifically, the methods are directed towards reducing viral infection, or towards reducing the phenotypic expression of endogenous plant gene.

WO 00/49035 discloses a method for silencing the expression of an endogenous gene in a cell, the method involving overexpressing in the cell a nucleic acid molecule of the endogenous gene, wherein the overexpression of the nucleic acid molecule of the endogenous gene and the antisense molecule in the cell silences the expression of the endogenous gene.

U.S. Pat. No. 6,423,885 discloses methods for reducing the phenotypic expression of a nucleic acid of interest in plant cells, by providing aberrant, preferably unpolyadenylated, target-specific RNA to the nucleus of the host cell.

US Application No. 2002/0169298 discloses a method for producing transgenic cereal plants resistant to Barley Yellow Dwarf Virus, particularly in the presence of co-infecting Cereal Yellow Dwarf Virus, by stably integrating into the cells of the transgenic plant a chimeric gene enabling the transcription of a viral RNA dependent RNA polymerase comprising both sense and antisense RNA, capable of pairing and forming a double stranded RNA molecule or hairpin RNA.

The methods described hitherto are all directed to silencing the expression of a target gene within eukaryotic cells, particularly plant cells. To prevent the development of a parasite in or on a plant, silencing an essential parasite gene, particularly a gene involved with the early stages of the parasite establishment, is desired. Gene silencing employing the method of introducing dsRNA was demonstrated in the nematode *C. elegans* by direct administration of the dsRNA to the parasite. The dsRNA was administered to the worm by various modes of delivery such as microinjection, feeding on *Escherichia coli* expressing dsRNA or simply soaking the animals in dsRNA preparations (Fire, A. Xu S. Montgomery M. K. Kostas S. A. Driver S. E. Mello C. C. 1998. Nature 391:806-811; Tabara, H. et al., supra).

WO 04/005485, corresponding to US Patent Application No. 2004/0098761 to Trick et al. relates to compositions and methods for controlling nematode infestation of plants or animals. Specifically, the invention discloses transgenic plants transformed with RNAi targeted to an RNA sequence selected from the group consisting of nematode Major sperm protein (MSP), RNA polymerase II and Chitin synthase. The invention is exemplified by reduction in the number of nematode cysts in transgenic plants expressing RNAi targeted to MSP gene.

Nematode infestation is responsible only for a portion of the damage caused by plant parasites to agricultural crops. Other parasites, including insects and fungi feeding on the plant cytoplasm adversely affect the yield of food crops as well as of ornamental crops. Moreover, the growing demand to employ practices suitable for sustainable agriculture, requires the development of new means for parasite control in order to reduce the use of insecticides and fungicides, Thus, there is a recognized need for, and it would be highly advantageous to have methods of means for controlling plant parasite insects and fungi. Moreover, efficient control of plant parasites requires means directed to arrest the parasite growth at an early developmental stage, so as to prevent its development in or on the plant.

SUMMARY OF THE INVENTION

The present invention provides compositions and methods for the production of plants resistant to parasites, specifically parasites that feed on the plant cytoplasm. Particularly, the present invention provides biotic methods to confer parasite resistance on a plant. The biotic methods provided by the present invention take advantage of the normal life cycle of the parasite, which includes cytoplasm consumption, to neutralize the parasites and to confer parasite resistance on a plant.

According to a first aspect, the present invention discloses a system utilizing small interfering RNAs (siRNAs) expressed in plants for the silencing of plant parasites.

Specifically, the present invention relates to parasites having a life cycle that normally includes a stage wherein they feed on the plant cell cytoplasm. siRNAs expressed in the plant cells are therefore ingested by the parasite and inhibit the expression of a parasite target gene encoding a product essential for the parasite development in or on the plant.

The present invention is based in part on the discovery that generation of siRNAs in the plant is useful for successfully silencing parasite gene expression. Expression of siRNAs complementary to parasite specific genes prevents the development, growth and propagation of the parasite in or on the plant, and thereby results in transgenic plants resistant to the parasites.

Thus, according to one aspect, the present invention provides a transgenic plant comprising at least one cell transformed with a DNA construct for generating siRNAs targeted to a gene of a cytoplasm-feeding plant parasite, wherein the plant is resistant to the development of the parasite in or on said plant.

It is to be understood that the practice of the present invention is not limited to any specific DNA construct, providing the construct is designed to express in the plant cell siRNA targeted to a parasite gene. According to some embodiments, the construct comprises nucleic acid sequences encoding a double stranded parasite RNA sequence, wherein the double stranded RNA silence the parasite target gene. The DNA construct may be designed to form double stranded RNA in various ways.

According to one embodiment, the DNA construct for generating siRNA targeted to a gene of a plant parasite comprises an expression cassette comprising:
(a) at least one plant expressible promoter operably linked to;
(b) a polynucleotide sequences encoding a double stranded RNA, comprising:
  i. a first nucleotide sequence of at least 20 contiguous nucleotides having at least 90% sequence identity to the sense nucleotide sequence of the target gene of the plant parasite; and
  ii. a second nucleotide sequence of at least 20 contiguous nucleotides having at least 90% sequence identity to the complementary sequence of the sense nucleotide sequence of said target gene of said plant parasite; and optionally
  iii. a transcription termination signal.

According to one currently preferred embodiment, the DNA construct for generating siRNA is in a form of a stem loop RNA, thus comprises an expression cassette comprising:
(a) at least one plant expressible promoter operably linked to;
(b) a polynucleotide sequences which yields a transcript comprising a stem-loop RNA, comprising:
  i. a first nucleotide sequence of at least 20 contiguous nucleotides having at least 90% sequence identity to the sense nucleotide sequence of the target gene of the plant parasite;
  ii. a second nucleotide sequence of at least 20 contiguous nucleotides having at least 90% identity to the complementary sequence of the sense nucleotide sequence of said target gene of said plant parasite; and
  iii. a spacer sequence; and optionally,
  iv. a transcription termination signal.

It is to be understood the compositions and methods of the present invention encompasses gene silencing of any parasite which consumes plant cytoplasm, regardless the way of feeding, including parasites sucking the plant sap, parasites proliferating within the plant cell, parasites invading into the plant cell via specialized structures and the like.

According to certain embodiments, the cytoplasm-feeding plant parasite is selected from the group consisting of, but not limited to, an insect, a nematode and a fungus.

According to one embodiment, the cytoplasm-feeding insect is selected from the group consisting of *Hemiptera*, including whiteflies and aphids, and Acari, including mites and ticks. According to one currently preferred embodiment, the parasite is the tobacco whitefly *Bemisia tabaci*.

According to another embodiment, the plant parasite is a nematode. According to yet another embodiment, the nematode is of the species *Meloidogyne*. According to one currently preferred embodiment, the nematode is *Meloidogyne javanica*.

According to some embodiments, the first and the second nucleotide sequences are operably linked to the same promoter. In other embodiments, each of the first and the second nucleotide sequences is operably linked to a separate promoter, wherein the separate promoters may be the same or different.

The selection of a suitable promoter will be dictated by the type of host cell in which it is intended to use the expression cassette of the invention. Suitable promoters that function in bacteria, yeast, and plants are all well known in the art. The promoter may further be selected on the basis of transcriptional regulation that it provides. Transcriptional regulation may include enhancement of transcriptional activity, inducibility, tissue specificity, and developmental stage specificity. In plants, promoters of plant, viral or synthetic origins that are inducible, constitutively active, temporally regulated and spatially regulated have been described.

Commonly used constitutive promoters include the CaMV 35S promoter, the enhanced CaMV 35S promoter, the Figwort Mosaic Virus (FMV) promoter, the mannopine synthase (mas) promoter, the nopaline synthase (nos) promoter, and the octopine synthase (ocs) promoter. Useful inducible promoters include Pathogenesis related (PR) promoters induced by salicylic acid or polyacrylic acids (PR-1), heat-shock promoters, a nitrate-inducible promoter derived from the spinach nitrite reductase sequence, hormone-inducible promoters, and light-inducible promoters associated with the small subunit of RuBP carboxylase and light harvesting chloroplast binding protein (LHCP) families.

According to one embodiment, the plant-expressible promoter is a constitutive promoter. Preferably, the parasite gene targeted for silencing is not endogenous to the plant genome. When such gene product shows no effect on the normal plant life cycle, a constitutive promoter is preferably used, resulting in resistant plants with no prerequisite for an induction signal. According to one currently preferred embodiment, the plant-expressible constitutive promoter is a CaMV 35S promoter.

According to another embodiment, the plant-expressible promoter is a tissue specific promoter. Tissue specific promoters are advantageous in that they limit the expression of the foreign gene to the area where its activity is required, reducing the risk of obtaining gene products which are undesired or lethal to other tissues. As used herein "tissue specific" includes root, tuber, vascular tissue, mesophyl tissue, stem, stamen, fruit, seed or leaf specific promoters.

According to one embodiment, the tissue specific promoter is a leaf-specific promoter. Many species of plant parasites are found in or on the plant leaves. The parasite either colonizes within the leaf cells or fed by interrupting the leaf tissue and sucking the plant sap and cytoplasm. Limiting the expression of the siRNAs to the leaf can therefore provide transgenic plants resistant to the leaf-parasite without affecting other plant parts. Leaf-specific promoters are known in the art. For example, leaf specific promoter can be selected from the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588).

According to another embodiment, the tissue specific promoter is a root specific promoter. The majority of plant parasitic nematodes attack plant roots rather than aerial tissues; thus, limiting the expression of siRNAs according to the present invention to root tissues will not reduce the efficacy of the resistance acquired by the plants. Root specific promoters are exemplified by, but are not limited to, the promoter from the b1-tubulin gene of *Arabidopsis* (TUB-1); the promoter from the metallothionein-like gene from *Pisum sativum* (PsMT$_A$); the RPL16A promoter from *Arabidopsis thaliana*; the ARSK1 promoter from *A. thaliana*; the AKTI gene promoter of *A. thaliana*; and the promoter of the *Lotus japonicus* LJAS2 gene.

The tissue specific promoter can be also an inducible promoter which is inactive in a plant in the absence of any parasite infection, but which exhibits a degree of "up-regulation" at an infected locale once infection occurs, or it can be active only in the presence of parasites.

According to one embodiment, the first nucleotide sequence includes a sequence of at least 20 contiguous nucleotides which are at least 95% identical to the sequence of the sense nucleotide sequence of the parasite target gene. According to further embodiment, the first nucleotide sequence includes a sequence of at least 20 contiguous nucleotides which are 100% identical to the sequence of the sense nucleotide sequence of the parasite target gene.

According to one embodiment, the second nucleotide sequence includes a sequence of at least 20 contiguous nucleotides which are at least 95% identical to the sequence of the complement of the sense nucleotide sequence of the parasite target gene. According to further embodiment, the second nucleotide sequence includes a sequence of at least 20 contiguous nucleotides which are 100% identical to the sequence complementary to the sense nucleotide sequence of the parasite target gene.

According to one embodiment, the first nucleotide sequence comprising the nucleotide sequence of at least 20 contiguous nucleotides having at least 90% sequence identity to the sense nucleotide of the parasite target gene further comprises at least one and maximum ten additional polynucleotide sequences each of said additional nucleotide sequences being of at least 20 contiguous nucleotides having at least 90% sequence identity to the sense sequence of the gene of the plant parasite.

There is no upper limit to the length of the first and the second nucleotide sequences that can be used, such that the construct of the present invention can include nucleotide sequences of varying lengths, including those from about 20 nucleotides to the full length of the target RNA. Preferably, the length of the first and the second nucleotide according to the present invention is about 1,000 nucleotides in length, more preferably about 500 nucleotides in length. According to another embodiment, the length of the first and the second nucleotide is about 22 nucleotides in length.

According to a preferred embodiment, the parasite target gene is not a plant endogenous gene. In a more preferred embodiment, the gene product has no effect on the normal plant cell life cycle. According to yet another embodiment, the selected parasite target gene has been shown to be affected by siRNAs.

According to certain embodiments, the parasite target gene is associated with early developmental stages of the parasite in or on the plant. The stages of parasite development in or on a plant depend on the parasite type as well as on the plant on which it is established. Under any developmental pattern, the earlier the parasite growth is arrested, the less is the damage caused to the plant. Thus, silencing a gene involved in the early developmental stages of the parasite in or on the plant is highly advantageous. Identification of genes involved in the early developmental stages of a parasite in or on a plant is can be performed utilizing computerized databases as is known to a person skilled in the art.

According to one embodiment, the plant parasite target gene is *B. tabaci* gene encoding a voltage-gated sodium channel (designated herein after as "*B. tabaci* vgsc gene"), the gene comprising the nucleotide sequence set forth in SEQ ID NO:1 (FIG. 1; Accession number AJ440728).

According to one currently preferred embodiment, the first nucleotide sequence comprises a nucleotide sequence having 90% identity, preferably 95%, more preferably 100% identity to the nucleotide sequence set forth in SEQ ID NO:1 or a fragment thereof.

According to another currently preferred embodiment, the second nucleotide sequence comprises a nucleotide sequence having 90% identity, preferably 95%, more preferably 100% identity to the complement of the nucleotide sequence set forth in SEQ ID NO:1 or a fragment thereof.

According to still another embodiment, the plant parasite target gene is *B. tabaci* gene encoding a eukaryotic translation initiation factor 5A (designated herein after as "*B. tabaci* eIF5A gene"). The present invention describes for the first time the isolation of the *B. tabaci* eIF5A gene, comprising the nucleotide sequence set forth in ID NO:2 (FIG. 2).

According to one currently preferred embodiment, the first nucleotide sequence comprises a nucleotide sequence having 90% identity, preferably 95%, more preferably 100% identity to the nucleotide sequence set forth in ID NO:2 or a fragment thereof.

According to another currently preferred embodiment, the second nucleotide sequence comprises a nucleotide sequence having 90% identity, preferably 95%, more preferably 100% identity to the complement of the nucleotide sequence set forth in SEQ ID NO:2 or a fragment thereof.

According to one embodiment, the early developmental stage target gene of a plant parasite is a *M. javanica* collagen gene col-5, having the nucleotide sequence set forth in SEQ ID NO:3 (FIG. 3; GeneBank gi: 15077110; Accession number AF289026).

According to one currently preferred embodiment, the first nucleotide sequence comprises a nucleotide sequence having 90% identity, preferably 95%, more preferably 100% identity to the nucleotide sequence of *M. javanica* collagen gene col-5 from position 704 to 1521 set forth in SEQ ID NO:3, the fragment designated herein as SEQ ID NO:4 (FIG. 3) or a fragment thereof.

According to another currently preferred embodiment, the second nucleotide sequence comprises a nucleotide sequence having 90% identity, preferably 95%, more preferably 100% identity to the complement of the nucleotide sequence set forth in SEQ ID NO:4 or a fragment thereof.

According to one embodiment, the structure of the inhibitory RNA molecule comprises further to the first and the second nucleotide sequences a spacer sequence, thus the double stranded RNA is in a form of stem-loop RNA (hairpin RNA, hpRNA). In a preferred embodiment, the length of the spacer sequence is ⅕ to ⅒ of the length of the first and the second nucleotides.

According to one embodiment, the spacer comprises a nucleotide sequence derived from a gene intron to enhance silencing of the parasite target gene. According to one currently preferred embodiment, the spacer comprises a nucleotide sequence comprising an intron from *Arabidopsis thaliana* Myb-related transcription factor cca-1 gene (gi: 4090568; Accession Number U79156, SEQ ID NO:5). According to one currently most preferred embodiment, the spacer comprises a fragment of SEQ ID NO:5, from position 3273 to position 3379, the fragment designated herein as SEQ ID NO:6 (FIG. 4).

Optionally, the construct encoding the siRNA comprises a transcription termination signal. According to one embodiment, the transcription termination signal is NOS terminator.

Another option is to incorporate a selectable marker into the construct encoding the siRNA, such that only transgenic plants can germinate and develop. According to one embodiment, the selection marker is a gene inducing antibiotic resistance within the plant.

Any desired plant may be selected to produce the transgenic plants of the present invention. Non limiting examples include soybean, wheat, oats, sorghum, cotton, tomato, potato, tobacco, pepper, rice, corn, barley, Brassica, Arabidopsis, sunflower, poplar, pineapple, banana, turf grass, and pine. Many plant species can be transformed with heterologous genes. However, efficient transformation methods are not always available for commercial plant varieties. Traditional breeding systems known to a person skilled in the art can be used to obtain parasite resistant commercial plants, wherein a non-commercial transgenic plant variety according to the present invention is bred with a commercially valuable variety.

According to one currently preferred embodiment, the transgenic parasite-resistant plant is a tobacco plant. According to another currently preferred embodiment, the transgenic parasite-resistant plant is a banana plant.

The DNA construct may be incorporated into a plant transformation vector which used to transform wild type plants, which is incorporated into at least one plant cell.

According to additional aspects, the present invention provides methods for producing a plant resistant to parasites. The methods provided utilize the natural life cycle of the parasite, which includes a stage of feeding on the plant cytoplasm, using siRNAs expressed by a plant cell to impose gene silencing in the parasite. The present invention shows for the first time that expression of siRNAs by the plant cell silence the parasite gene to which the siRNAs was targeted.

According to preferred embodiments of the invention, the affected gene is essential for parasite development, growth and propagation so that its silencing prevents parasite growth in or on the plant, thereby providing a resistant plant. According to another preferred embodiment, the affected gene is involved in an early developmental stage of the parasite in or on the plant. According to yet additional preferred embodiment, the affected gene is expressed in an early developmental stage of the parasite in or on the plant.

According to one embodiment, the present invention provides a method of producing a transgenic parasite-resistant plant, comprising introducing into at least one cell of a plant a DNA construct for generating siRNAs targeted to a gene of the plant parasite thereby producing a transgenic plant resistant to the development of said parasite in or on the plant.

According to another embodiment, the present invention provides a method for producing a population of transgenic plants comprising selecting a transgenic plant comprising at least one cell transformed with a DNA construct for generating siRNAs targeted to a gene of a plant parasite; and selfing the transgenic plant or crossing the transgenic plant to another plant to obtain progeny comprising at least one cell transformed with the DNA construct.

According to yet another aspect, the present invention provides a method for enhancing the production of siRNAs within a plant cell, the method being useful when the parasite target gene is not a plant endogenous gene, said method leading to enhanced resistance of the plant to the parasite. The enhanced production of siRNAs is achieved by transforming a plant that expresses the double stranded RNA according to the present invention with an additional DNA construct comprising a plant expressible promoter operably linked to a fragment of the parasite target gene. As a result, the plant cells contain both—siRNAs, which result from the cleavage of the stem loop dsRNA, and a cognate mRNA of a fragment of the parasite target gene. The siRNAs serve as primers that recognize the mRNA, promoting the formation of additional dsRNAs thus amplifying the production of siRNAs.

According to one embodiment, the present invention provide a method for enhancing the production of siRNAs comprising:
  (a) providing a plant expressing a first DNA construct for generating siRNA comprising the expression cassette according to the present invention;
  (b) transforming said plant with a second DNA construct, the second DNA construct comprising:
    i. a plant expressible promoter; operably linked to
    ii. a sense nucleotide sequence of about 50-2000 nucleotides derived from the gene of the plant parasite comprising at least 20 contiguous nucleotides having at least 90% identity to the first nucleotide sequence of the expression cassette according to (a); and optionally
    iii. a transcription termination signal.

According to one embodiment, the sense nucleotide sequence derived from the gene of the plant parasite is of 50-2,000 nucleotides in length, preferably 100-500 nucleotides in length.

According to another embodiment, the sense nucleotide sequence derived from the gene of the plant parasite comprises at least 20 contiguous nucleotides having at least 90% identity, preferably 95%, more preferably 100% identity to the first nucleotide sequence of the expression cassette according to the present invention.

Transformation of plants with a DNA construct may be performed by various means, as is known to one skilled in the art. Common methods are exemplified by, but are not restricted to, *Agrobacterium*-mediated transformation, microprojectile bombardment, pollen mediated transfer, plant RNA virus mediated transformation, liposome mediated transformation, direct gene transfer (e.g. by microinjection) and electroporation of compact embryogenic calli. According to one embodiment, resistant plants are produced using *Agrobacterium* mediated transformation.

Transgenic plants comprising the construct of the present invention may be selected employing standard methods of molecular genetic, known to a person of ordinary skill in the art. According to one embodiment, the transgenic plants are selected according to their resistance to antibiotic. According to certain embodiments, the antibiotic serving as a selectable marker is one of the group consisting of cefotaxime, vancomycin and kanamycin.

According to another embodiment, the transgenic plants are selected according to their resistance to a parasite selected from the group consisting of an insect, a nematode and a fungus. According to one embodiment, the insect is selected from the group consisting of *Hemiptera*, including whiteflies and aphids, and Acari, including mites and ticks. According to currently preferred embodiment, the insect is *B. tabaci*. According to another currently preferred embodiment, the nematode is *M. javanica*. According to one embodiment selection is confirmed by deliberate infection of the plant with the parasite in question. Plants showing low infection rate, according to an infection scale specific for each parasite, are defined as plants resistant to the parasite.

According to another aspect the present invention relates to the transgenic plants generated by the methods of the present invention as well as to their seeds, fruits, roots and other organs or isolated parts thereof. The expression cassette according to the present invention is integrated and expressed by the genome of the plants, resulting in the inability of the parasite to develop, grow and propagate in or on the plant.

According one embodiment the present invention provides plants and plant populations comprising the construct of the invention stably integrated into the genome of the cells of the plant, wherein said plants are resistant to parasite development.

According to one embodiment, the plants are resistant to cytoplasm-feeding parasites. According to one embodiment, the parasite is selected from the group consisting of an insect, a nematode and a fungus. According to one embodiment, the plant is resistant to a parasite insect selected from the group consisting of *Hemiptera*, including whiteflies and aphids, and Acari, including mites and ticks. According to one currently preferred embodiment, the plant is resistant to the tobacco whitefly *Bemisia tabaci*. According to another embodiment, the plant is resistant to a nematode. According to one currently preferred embodiment, the plant is resistant to *Meloidogyne javanica*.

These and additional features of the present invention are explained in greater detail in the figures, description and claims below.

BRIEF DESCRIPTION OF THE FIGURES

FIG. 1 describes (A) the partial sequence of *B. tabaci* gene encoding voltage-gated sodium channel (SEQ ID NO:1, Accession No. AJ440728), and a schematic description of the silencing construct of *B. tabaci* vgsc gene (B).

FIG. 2 describes the partial nucleotide sequence of *B. tabaci* eIF5A gene (SEQ ID NO:2).

FIG. 3 describes the nucleotide sequence of *M. javanica* col-5 gene (SEQ ID NO:3). Underlined between arrows is the nucleotide sequence amplified for the production of the stem region of col-5 hpRNA (SEQ ID NO:4).

FIG. 4 describes the nucleotide sequence of *A. thaliana* cca-1 gene (SEQ ID NO:5). Underlined between arrows is the nucleotide sequence amplified for the production of the spacer region of col-5 hpRNA (SEQ ID NO:6).

FIG. 6 shows a schematic description of a construct according to the present invention (A) and its expression by transgenic plants (B).

DETAILED DESCRIPTION OF THE INVENTION

Figures 5A, 5B:
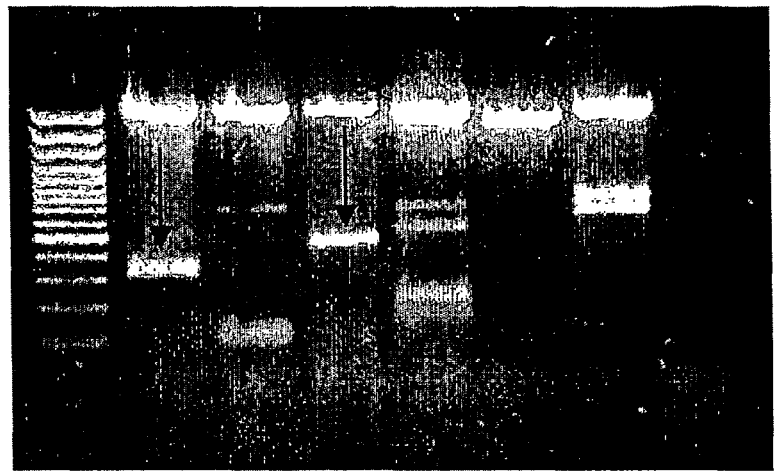
FIG. 5A shows the position of cDNA fragments of eIF5A cloned in the vector pGEM T-Easy and treated with EcoRI in a 1% agarose gel.
FIG. 5B shows the alignment of the protein encoded by the *B. tabaci* eIF5A gene (SEQ ID NO:25) with eIF5A of *Drosophila yakuba* (SEQ ID NO:26, Accession No. AAR10094.1)

The present invention relates to biotic resistance of plants to parasites. The present invention provides compositions and methods for producing plants resistant to parasites, specifically parasites the life cycle of which includes feeding on the plant cytoplasm.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Definitions

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower petal, fruit, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant organ or a plant tissue.

As used herein, the term "plant parasite" refers to an organism that lives in or on the plant without benefiting the host plant. Particularly, as used throughout the present invention, the term plant parasite refers to insects, nematodes and fungi which are feeding on the host plant nutrients. The term "cytoplasm-feeding parasite" refers to a parasite that in at least one stage of its normal life cycle its nourishment comprises plant cytoplasm.

The terms "parasite resistant plant" and "plant resistant to a parasite" refer to a plant having an increased tolerance to a parasite compared to a non-resistant (susceptible) plant. The increased tolerance is examined by deliberate infection of the plant with the parasite in question. Plants showing lower infection rate compared to susceptible plant, according to an infection scale specific for each parasite, are defined as plants resistant to the parasite.

The term "gene" refers to a nucleic acid (e.g., DNA or RNA) sequence that comprises coding sequences necessary for the production of RNA or a polypeptide. Functional polypeptide can be encoded by a full-length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene, wherein a genomic form or clone of a gene contains the coding region interrupted with non-coding sequences termed "introns" or "intervening regions" or "intervening sequences." Introns are removed or "spliced out" from the nuclear or primary transcript, and therefore are absent in the messenger RNA (mRNA) transcript.

The term "nucleic acid" as used herein refers to RNA or DNA that is linear or branched, single or double stranded, or a hybrid thereof. The term also encompasses RNA/DNA hybrids.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The terms "heterologous gene" or "chimeric genes" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous plant genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed). A plant gene endogenous to a particular plant species (endogenous plant gene) is a gene which is naturally found in that plant species or which can be introduced in that plant species by conventional breeding.

The term "transgenic" when used in reference to a plant or fruit or seed (i.e., a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in at least one of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "loop sequence" refers to a nucleic acid sequence that is placed between two nucleic sequences that are complementary to each other and which forms a loops when the complementary nucleic acid sequences hybridize to one another.

The term "RNA interference" or "RNAi" refers to the silencing or decreasing of gene expression by interfering RNA (iRNA) or small interfering RNAs (siRNAs). It is the process of sequence-specific, post-transcriptional gene silencing in animals and plants, initiated by iRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

According to a first aspect the present invention discloses a system utilizing small interfering RNAs expressed in plants for the silencing of parasite specific genes, wherein the parasite consumes plant cytoplasm in the normal course of its life cycle. According to some embodiments the present invention provides a system utilizing small interfering RNAs expressed in plants for the silencing of genes specific to a certain developmental stage. According to additional embodiments the present invention provides a system utilizing small interfering RNAs expressed in plants for the silencing of specific genes essential to the early development of a parasite in or on the plant, which are not endogenous plant genes.

The phenomenon of RNAi is triggered by double stranded (dsRNA). At least one strand of the double stranded region of an iRNA is substantially homologous to, or substantially complementary to the target RNA molecule. To obtain cells with dsRNA, an exogenous dsRNA may be administered to whole animals as was demonstrated, for example, in *C. elegans*. Alternatively, transgenic organisms may express endogenous dsRNA. dsRNA may be generated from either two opposing promoters, or in a form of a hairpin RNA (hpRNA) structure that is composed of sense and anti-sense sequences separated by a loop. Initiation of silencing occurs upon cleavage of the dsRNA into small interfering RNAs (siRNAs), 21-23 nucleotides long, by an RNase III enzyme called dicer. After processing by dicer, the siRNAs associate with a multi-component complex, the RNA-induced silencing complex (RISC). siRNA duplex undergoes unwinding, and target to the complementary RNA sequence on the target cognate mRNA. As a result, RISC recognizes and cleaves the target mRNA. This system allows silencing of specific genes by introducing an iRNA of a sequence of interest.

According to one aspect, the present invention provides compositions and methods for generating parasite-resistant plants. The present invention shows for the first time that introducing to a plant an expression cassette comprising a polynucleotide sequence encoding for RNA of a plant parasite gene in a form of a double stranded RNA, specifically in the form of hairpin RNA, interrupt the expression of the complementary gene within the parasite. Where the gene is essential to the parasite development, its silencing result in the inability of the parasite to develop in or on the plant.

According to one aspect, the present invention provides a transgenic plant comprising at least one cell transformed with a DNA construct for generating siRNAs targeted to a gene of a plant parasite, wherein the plant is resistant to the development of the parasite in or on said plant.

According to one embodiment, the plant parasite is a cytoplasm-feeding parasite. The methods and means provided by the present invention are adequate for silencing target genes of any plant parasite which, during the normal course of its development on or in the plant, consumes plant cytoplasm.

According to certain embodiments, the cytoplasm-feeding plant parasite is selected from the group consisting of, but not limited to, an insect, a nematode and a fungus.

According to one embodiment, the cytoplasm-feeding insect is selected from the group consisting of *Hemiptera*, including whiteflies and aphids, and Acari, including mites and ticks. According to one currently preferred embodiment, the parasite is the tobacco whitefly *Bemisia tabaci*.

According to another embodiment, the plant parasite is a nematode. According to yet another embodiment, the nematode is of the species *Meloidogyne*. According to one currently preferred embodiment, the nematode is *Meloidogyne javanica*.

According to one embodiment, the DNA construct comprises an expression cassette comprising a plant-expressible promoter operably linked to a DNA region which, when transcribed in the plant cell yields a double stranded RNA.

According to another embodiment, the expression cassette comprises the following:
(a) at least one plant expressible promoter operably linked to;
(b) a polynucleotide sequence encoding a double stranded RNA, comprising:
 i. a first nucleotide sequence of at least 20 contiguous nucleotides having at least 90% sequence identity to the sense nucleotide sequence of a gene of a plant parasite;
 ii. a second nucleotide sequence of at least 20 contiguous nucleotides having at least 90% sequence identity to the complementary sequence of the sense nucleotide sequence of said target gene of said plant parasite; and optionally
 iii. a transcription termination signal.

According to one currently preferred embodiment, the double stranded RNA is in the form of a stem-loop RNA, (hairpin RNA, hpRNA) thus the expression cassette comprises:
(a) at least one plant expressible promoter operably linked to;
(b) a polynucleotide sequences which yields a transcript comprising a stem-loop RNA, comprising:

i. a first nucleotide sequence of at least 20 contiguous nucleotides having at least 90% sequence identity to the sense nucleotide sequence of the target gene of the plant parasite;
ii. a second nucleotide sequence of at least 20 contiguous nucleotides having at least 90% identity to the complementary sequence of the sense nucleotide sequence of said target gene of said plant parasite; and
iii. a spacer sequence; and optionally,
iv. a transcription termination signal.

As used herein an expression cassette is a polynucleotide molecule comprising at least one polynucleotide sequence that is expressed in a host cell or organism. Typically such expression is under the control of certain cis acting regulatory elements including constitutive, inducible or tissue-specific promoters, and enhancing elements. Common to the art, such polynucleotide sequence(s) are said to be "operably linked to" the regulatory elements. Expression cassettes typically also include eukaryotic or bacterial derived selectable markers that allow for selection of eukaryotic cells containing the expression cassette. These can include, but are not limited to, various genes which confer antibiotic resistance and which are well known in the art.

For many applications it is required that the expression cassette described herein will be integrated in a DNA construct. Such constructs are well known in the art, are commercially available and may include additional sequences, such as, for example, a cloning site, one or more prokaryote or eukaryote marker genes with their associated promoters for selection of prokaryotic cells containing the expression cassette, one or more prokaryotic origins of replication, one or more translation start sites, one or more polyadenylation signals, and the like.

As used herein, the term "expression of a nucleotide sequence" refers to the process wherein a DNA region which is operably linked to appropriate regulatory regions, particularly to a promoter region, is transcribed into an RNA which is biologically active i.e., which is either capable of interaction with another nucleic acid or which is capable of being translated into a polypeptide or protein.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The nucleotide sequence of the expression cassette of the present invention can be a full-length gene or a part thereof. As used herein, the term "homology" when used in relation to nucleic acid sequences refers to a degree of similarity or identity between at least two nucleotide sequences. There may be partial homology or complete homology (i.e., identity). "Sequence identity" refers to a measure of relatedness between two or more nucleotide sequences, expressed as a percentage with reference to the total comparison length. The identity calculation takes into account those nucleotide residues that are identical and in the same relative positions in their respective sequences. A gap, i.e. a position in an alignment where a residue is present in one sequence but not in the other is regards as a position with non-identical residues.

Homology is determined for example using Gapped BLAST-based searches (Altschul et. al. 1997. Nucleic Acids Res. 25:3389-3402) and "BESTFIT".

As used herein, "a complement of a nucleotide sequence" is the nucleotide sequence which would be capable of forming a double stranded DNA molecule with the nucleotide sequence, and which can be derived from the nucleotide sequence by replacing the nucleotide through their complementary nucleotide according to Chargaff's rules (AT; GC) and reading in the 5' to 3' direction, i.e. in opposite direction of the nucleotide sequence.

As used herein, nucleotide sequence of RNA molecule may be identified by reference to DNA nucleotide sequence of the sequence listing. However, the person skilled in the art will understand whether RNA or DNA is meant depending on the context. Furthermore, the nucleotide sequence is identical except that the T-base is replaced by uracil (U) in RNA molecule.

According to certain embodiments, the first and the second nucleotide sequences are transcribed as two separate strands, which are at least partially complementary, thus capable of forming dsRNA. When the dsRNA is thus produced, the DNA sequence to be transcribed is flanked by two promoters, one controlling the transcription of the first nucleotide sequence, and the other that of the second, complementary nucleotide sequence. These two promoters may be identical or different. According to certain other embodiments, the first and the second nucleotide sequences are operably linked to the same promoter.

Plant expressible promoters are known in the art. The selection of a suitable promoter will be dictated by the type of host cell in which it is intended to use the expression cassette of the invention. The promoters may be constitutive, inducible, tissue-specific, or developmentally regulated. Promoter hybrids can also be constructed to enhance transcriptional activity (e.g., U.S. Pat. No. 5,106,739), or to combine desired transcriptional activity and tissue specificity.

The promoters to be used in the present invention will be selected according to their transcriptional regulation. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. An "inducible" promoter is one which is capable of directing a level of transcription of an operably linked nucleic acid sequence in the presence of a stimulus (e.g., heat shock, chemicals, light, etc.), which is different from the level of transcription of the operably linked nucleic acid sequence in the absence of the stimulus.

Promoters often used for constitutive gene expression in plants include the CaMV 35S promoter, the enhanced CaMV 35S promoter, the Figwort Mosaic Virus (FMV) promoter, the mannopine synthase (mas) promoter, the nopaline synthase (nos) promoter, and the octopine synthase (ocs) promoter.

A suitable inducible promoter may be selected from genes that are induced during a plant defense response against a parasite infection. For example, a fungal infection triggers an induction of a large number of pathogenesis-related (PR) proteins by the infected plant (for example, Linthorst. H. J. Danhash, N. Brederode, F. T. Van Kan, J. A. De Wit, P. J. Bol, J. F. 1991. Mol Plant Microbe Interact. 4:586-92). The promoters of these PR sequences may be obtained and utilized in the present invention. Isolation of these PR promoters has been reported from potato plants (e.g., Matton, D. P. and Brisson, N. 1989. Mol Plant Microbe Interact. 2:325-31) and tobacco plants. Other inducible promoters are heat-shock promoters, a nitrate-inducible promoter derived from the spinach nitrite reductase sequence, hormone-inducible promoters, and light-inducible promoters associated with the small subunit of RuBP carboxylase and light harvesting chloroplast binding protein (LHCP) families.

Promoters having particular utility in the present invention include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco; corn sucrose synthetase 1; corn alcohol dehydrogenase 1; corn light harvesting complex and corn heat shock protein promoters; the chitinase promoter from *Arabidopsis*; the LTP (Lipid Transfer Protein) promoters from broccoli; petunia chalcone isomerase; bean glycine rich protein 1; and potato patatin promoters; the ubiquitin promoter from maize; the sugarcane badnavirus promoter; the rice RC2 promoter; and the rice actin promoter. All of these promoters have been used to create various types of DNA constructs that have been expressed in plants. See, for example, International Patent Publication No. WO 84/02913 in this regard.

According to one embodiment, the plant-expressible promoter is a constitutive promoter. Constitutive promoters are used when the parasite target gene is not a plant endogenous gene, and when the gene product shows no effect of the normal life cycle of the plant, specifically when the gene product has no deleterious effect on the plant cell. When these criteria are, met, using a constitutive promoter is preferable in that it results in a plant resistant to parasite, wherein the resistance is not dependent on any induction requirements. According to one currently preferred embodiment, the plant-expressible constitutive promoter is a CaMV 35S promoter.

According to another embodiment, the plant-expressible promoter is a tissue specific promoter. Using tissue specific promoters restricts the expression of the chimeric gene to the tissue where the promoter is operable, reducing the risk of deleterious gene products in other tissues. The term "tissue specific" as it applies to a promoter refers to a promoter that is capable of directing selective expression of a nucleotide sequence of interest to a specific type of tissue (e.g., root tissue) in the relative absence of expression of the same nucleotide sequence of interest in a different type of tissue (e.g., leave tissue). As used herein "tissue specific promoters" refers to root (Keller, B. Lamb, C. J. 1989. Genes Devel. 3:1639-1646), tuber, vascular tissue (Peleman, J. Saito, K. Cottyn, B. Engler, G. Seurinck, J. Van Montagu, M. Inze, D. 1989 Gene 84:359-369), mesophyl tissue (such as the light-inducible Rubisco promoters), stem (Keller, B. Sauer, N. and Lamb, C J. 1988. EMBO J. 7:3625-3633), stamen (International Patent Publication Nos. WO 89/10396; WO 92/13956), fruit, seed or leaf specific promoters (Hudspeth, R. L. and Grula, J. W. 1989. Plant Mol Biol 12: 579-589).

According to yet another embodiment, the tissue specific promoter is a leaf-specific promoter. Most of the plant parasite insects, and many plant parasite fungi are found in or on the plant leaves. The parasites invade into the leaf tissue, either to be establish within the plant cells or to nourish from the components of the plant cells. Limiting the expression of the siRNAs to the leaf can therefore provide transgenic plants resistant to the leaf-parasite without affecting other plant parts. Leaf-specific promoters are known in the art. For example, leaf specific promoter can be selected from the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588).

According to yet another embodiment, the plant-expressible promoter is a root specific promoter. The majority of plant parasitic nematodes attack plant roots rather than aerial tissues. Examples of root parasitic nematodes are species of the genera *Heterodera, Globodera, Meloidogyne, Hoplolaimus, Helicotylenchus, Rotylenchoides, Belonolaimus, Paratylenchus, Paratylenchoides, Radopholus, Hirschmanniella, Naccobus, Rotylenchulus, Tylenchulus, Hemicycliophora, Criconemoides, Criconemella, Paratylenchus, Trichodorus, Paratrichodorus, Longidorus, Paralongidorus, Rhadinaphelenchus, Tylenchorhynchus, Hemicriconemoides, Scutellonema, Dolichodorus, Gracilacus, Cacopaurus, Xiphinema* and *Thecavermiculatus*. Host ranges of these species include many of the world's crops and are defined elsewhere (Luc et al, Plant Parasitic Nematodes in Subtropical and Tropical Agriculture, CAB International, Wallingford, p629 (1990), Evans et al, Plant Parasitic Neematodes in Subtropical and Tropical Agriculture, CAB International, Wallingford, p648 (1993)).

Root specific promoters are exemplified by, but are not limited to, the promoter from the b1-tubulin gene of *Arabidopsis* (TUB-1). Northern blots have shown that the transcript of this gene accumulates predominantly in roots, with low levels of transcription in flowers and barely detectable levels of transcript in leaves (Oppenheimer et al, Gene, 63:87-102 (1988)); the promoter from the metallothionein-like gene from *Pisum sativum* (PsMT$_A$), which is abundant in roots with less abundant expression elsewhere (Evans et al, FEBS Letters, 262:29-32 (1990)); the RPL16A promoter from *Arabidopsis thaliana* (the RPL16A gene from *A. thaliana* encodes the ribosomal protein, L16, its expression being cell specific); the ARSK1 promoter from *A. thaliana* (the ARSK1 gene encodes a protein with structural similarities to seine/threonine kinases and is root specific); the AKTI gene promoter of *A. thaliana*, the gene encoding a putative inwardly-directed potassium channel preferentially in the peripheral cell layers of mature roots (Basset et al., Plant Molecular Biology, 29: 947-958 (1995) and Lagarde et al., The Plant Journal, 9: 195-203 (1996); and the promoter of the *Lotus japonicus* LJAS2 gene, a gene encoding a root specific asparagine synthetase (Waterhouse et al., Plant Molecular Biology, 30: 883-897 (1996).

The tissue specific promoter can be one which is inactive in a plant in the absence of any parasite infection, but which exhibits a degree of "up-regulation" at an infected locale once infection occurs, or it can be active only in the presence of parasites.

It will be appreciated that the longer the total length of the first nucleotide sequence is, the requirements for sequence identity to the sequence of the parasite target gene are less stringent. The total first nucleotide sequence can have a sequence identity of at least about 90% with the corresponding parasite target gene, as well as higher sequences identity of about 95% or 100%.

According to one embodiment, the first nucleotide sequence includes a sequence of at least 20 contiguous nucleotides which are at least 90% identical to the sequence of the sense nucleotide sequence of the parasite target gene. According to further embodiment, the first nucleotide sequence includes a sequence of at least 20 contiguous nucleotides which are 95% identical, preferably 100% identical to the sequence of the sense nucleotide sequence of the parasite target gene.

The length of the second (antisense) nucleotide sequence is largely determined by the length of the first (sense) nucleotide sequence, and may correspond to the length of the latter sequence. However, it is possible to use antisense sequences that differ in length by about 10%. Similarly, the nucleotide sequence of the antisense region is largely determined by the nucleotide sequence of the sense region, and may have a sequence identity of about 90% with the complement sequence of the sense region, as well as higher sequences identity of about 95% or 100%.

According to one embodiment, the second nucleotide sequence includes a sequence of at least 20 contiguous nucleotides which are at least 90% identical to the sequence of the complement of the sense nucleotide sequence of the parasite target gene, preferably 95% identical, more preferably 100% identical to the sequence complementary to the sense nucleotide sequence of the parasite target gene.

The first and the second nucleotide sequences can be of any length providing the sequences comprising at least 20 contiguous nucleotides. Thus, the first and the second nucleotide can comprise a portion of a gene, or the full length of the gene. According to some embodiments, the length of the nucleotides sequences is from 20 nucleotides to 1,000 nucleotides.

According to a preferred embodiment, the parasite target gene is not a plant endogenous gene. In a more preferred embodiment, the gene product has no effect on the normal plant cell life cycle. According to yet another embodiment, the selected parasite target gene has been shown to be affected by siRNAs.

According to one embodiment, the plant parasite target gene is *B. tabaci* gene encoding a voltage-gated sodium channel, comprising the nucleotide sequence set forth in SEQ ID NO:1 (FIG. 1: Accession number AJ440728).

According to one currently preferred embodiment, the first nucleotide sequence comprises a nucleotide sequence having 90% identity, preferably 95%, more preferably 100% identity to the nucleotide sequence set forth in SEQ ID NO:1 and fragments thereof.

According to yet another currently preferred embodiment, the second nucleotide sequence comprises a nucleotide sequence having 90% identity, preferably 95%, more preferably 100% identity to the complement of the nucleotide sequence set forth in SEQ ID NO:1 and fragments thereof.

According to still another embodiment, the plant parasite target gene is *B. tabaci* gene encoding a eukaryotic translation initiation factor 5A. As described in the Example section herein below, the present invention now discloses a nucleotide sequence of eIF5A gene isolated from *B. tabaci*. The eIF5A cDNA (SEQ ID NO:2) was cloned using degenerate primers designed according to a consensus sequence found between the nucleotide sequences of eIF5A isolated from various organisms, as described herein below.

According to one currently preferred embodiment, the first nucleotide sequence comprises a nucleotide sequence having 90% identity, preferably 95%, more preferably 100% identity to the nucleotide sequence set forth in SEQ ID NO:2 and fragments thereof.

According to yet another embodiment, the second nucleotide sequence comprises a nucleotide sequence having 90% identity, preferably 95%, more preferably 100% identity to the complement of the nucleotide sequence set forth in SEQ ID NO:2 and fragments thereof.

According to certain embodiments, parasite genes selected as a target for silencing are genes that are active in early developmental stages of the parasite. As used herein, "early developmental stages" relates to the primary steps of the parasite development in or on the plant cells. According to one embodiment, the parasite is a nematode, and the early developmental stage is defined as J1 developing eggs, and J2 worms. Preferably, the parasite target genes are not endogenous plant genes; therefore, disrupting the expression of the target gene interferes with the development of the parasite but has no effect on the plant. Preferably, disrupting the expression of the target gene is lethal to the parasite. Such genes may be found in any plant parasite. According to some embodiments, siRNAs according to the present invention are targeted to early developmental gene of a parasite selected from the group consisting of cytoplasm-feeding plant parasite, particularly an insect, a nematode or a fungus. According to one currently preferred embodiment, the siRNAs are targeted to a gene involved in an early developmental stage of a nematode.

According to one embodiment, the early developmental stage target gene of a plant parasite is a *M. javanica* collagen gene col-5, having the nucleotide sequence set forth in SEQ ID NO:3 (FIG. 3; GeneBank gi: 15077110; Accession number AF289026).

According to one currently preferred embodiment, the first nucleotide sequence comprises a nucleotide sequence having 90% identity, preferably 95%, more preferably 100% identity to the nucleotide sequence of *M. javanica* collagen gene col-5 from position 704 to 1521 set forth in SEQ ID NO:3, the fragment designated herein as SEQ ID NO:4 (FIG. 3) and fragments thereof.

According to yet another currently preferred embodiment, the second nucleotide sequence comprises a nucleotide sequence having 90% identity, preferably 95%, more preferably 100% identity to the nucleotide sequence set forth in SEQ ID NO:4 and fragments thereof.

Nucleotide molecules which cross-hybridizes to (i) a nucleic acid having a nucleotide sequence selected from SEQ ID NO:1, SEQ ID NO:2 and SEQ ID NO:3 or (ii) the complement of a nucleotide sequence selected from SEQ ID NO:1, SEQ ID NO:2 and SEQ ID NO:3 and fragments thereof are also within the scope of the present invention.

As used herein, the terms "stringent conditions" or "stringency", refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. to about 25° C. below the melting temperature of the probe). One or more factors may be varied to generate conditions of either low or high stringency. Hybridization and wash conditions are well known and are exemplified in Sambrook et al., Molecular cloning: A laboratory manual, Second Edition, Cold Spring Harbor, N.Y. 1989, particularly chapter 11. According to one embodiment, cross-hybridization is performed under moderate stringency of 1.0-2.0×SSC at 65° C.

The col-5 gene and the vgsc gene were identified by a comprehensive search for genes that were identified as essential for the parasite development. The col-5 gene was identified by specifically searching for a gene involved in an early stage of the nematode developmental in the plant, which was also demonstrated to be silenced and cause embryonic lethality in RNAi assay in the parasite. After this search, genes that exist in plants, and their silencing may have deleterious effects, were excluded from further assay.

Identification of other parasite target genes is readily performed according to the same approach, utilizing computerized databases as is known to a person skilled in the art, such as GenBank—

The principles by which a parasite target gene is selected are as follows: the product of the parasite gene is essential for the development of the parasite; preferably, the parasite gene was shown to be silenced by siRNA; more preferably, the parasite gene product is not deleterious to the normal life cycle of the plant; and optionally, the parasite gene is not an endogenous part of the plant genome.

According to some embodiments, the expression cassette according to the present invention is designed to express a stem-loop RNA, comprising further to the first (sense) and the second (antisense) nucleotide sequences a spacer polynucleotide sequence, located between the DNA region encoding the first and the second nucleotide sequences. The length of the spacer polynucleotide sequence may vary according to the specific structure of the stem-loop RNA. Typically, the ratio of the spacer length to the first and second nucleotide sequences length is in the range of 1:5 to 1:10.

According to one embodiment, the spacer comprises a nucleotide sequence derived from a gene intron to enhance silencing of the parasite target gene. According to one currently preferred embodiment, the spacer comprises a nucleotide sequence comprising an intron from *Arabidopsis thaliana* Myb-related transcription factor cca-1 gene (gi: 4090568; Accession Number U79156, SEQ ID NO:5). According to one currently most preferred embodiment, the spacer comprises a fragment of SEQ ID NO:5, from position 3273 to position 3379, the fragment designated herein as SEQ ID NO:6 (FIG. 4) and fragments thereof.

Constructs designed for transformation of nucleotide sequences typically also include eukaryotic or bacterial derived selectable markers that allow for selection of eukaryotic cells containing the construct of the invention. The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). These can include, but are not limited to, various genes which confer antibiotic resistance and which are well known in the art. According to one currently preferred embodiment, the selectable marker is a gene conferring resistance to an antibiotic selected from the group consisting of cefotaxime, vancomycin and kanamycin.

Optionally, the construct encoding the siRNA comprises a transcription termination signal. A variety of terminators that may be employed in the constructs of the present invention are well known to those skilled in the art. The terminator may be from the same gene as the promoter sequence or a different gene. According to one embodiment, the transcription termination signal is NOS terminator.

According to another aspect, the present invention provides methods for producing a plant resistant to parasites. The methods provided utilizes the natural life cycle of the parasite, which includes a stage of feeding on the plant cytoplasm, showing for the first time that siRNAs expressed by a plant cell impose gene silencing in the parasite. According to preferred embodiments of the invention, the affected gene is essential for the parasite development, so that its silencing prevents parasite growth in or on the plant, thereby providing a resistant plant. According to another preferred embodiment, the affected gene is essential to an early developmental stage of the parasite in or on the plant.

According to one embodiment, the present invention provides a method of producing a transgenic parasite resistant plant, comprising introducing into at least one cell of a plant a DNA construct for generating siRNAs targeted to a gene of a plant parasite thereby producing a transgenic plant resistant to the development of the parasite in or on the plant.

According to one embodiment, the expression cassette of the invention used in the above-described method comprises the following operably linked parameters:
  (a) at least one plant expressible promoter;
  (b) polynucleotide sequence encoding double stranded RNA, comprising
    (i) a first nucleotide sequence of at least 20 contiguous nucleotides having at least 90% sequence identity to the sense nucleotide sequence of a gene of a plant parasite;
    (ii) a second nucleotide of at least 20 contiguous nucleotides sequence having at least 90% identity to the complementary sequence of the sense nucleotide sequence of the gene of the plant parasite; and optionally
    (iii) a transcription termination signal.

As used herein the term "transformation" describes a process by which a foreign DNA, such as an expression cassette, enters and changes a recipient cell into a transformed, genetically modified or transgenic cell. Transformation may rely on any known method for the insertion of foreign nucleic acid sequences into a eukaryotic host cell. An expression cassette can be transiently expresses by a cell of a plant or stably incorporated in the genome of a plant cell. Gene transfer can be carried out for example with a vector that is a disarmed Ti-plasmid, comprising an expression cassette, and carried by *Agrobacterium* (See, for example, U.S. Pat. Nos. 4,940,838; 5,981,840; and 6,051,757).

Alternatively, any type of vector can be used to transform the plant cell, applying methods such as direct gene transfer (e.g., by microinjection or electroporation), pollen-mediated transformation (as described, for example, in European patent No. EP270356, International Patent Publication No. WO085/01856 and U.S. Pat. No. 4,684,611), plant RNA virus-mediated transformation (as described, for example, in European Patent No. EP067553 and U.S. Pat. No. 4,407,956), liposome-mediated transformation (as described, for example, in U.S. Pat. No. 4,536,475), and the like.

Other methods, such as microprojectile bombardment are suitable as well. Cells of monocotyledonous plants, such as the major cereals, can also be transformed using wounded and/or enzyme-degraded compact embryogenic tissue capable of forming compact embryogenic callus, or wounded and/or degraded immature embryos as described in International Patent Publication No. WO 92/09696. The resulting transformed plant cell can then be used to regenerate a transgenic plant in a conventional manner.

Those skilled in the art will appreciate that the various components of the DNA constructs and the transformation vectors described in the present invention are operatively linked, so as to result in expression of said nucleic acid or nucleic acid fragment. Techniques for operatively linking the components of the constructs and vectors of the present invention are well known to those skilled in the art. Such techniques include the use of linkers, such as synthetic linkers, for example including one or more restriction enzyme sites.

As exemplified herein below, the transgenic plants of the present invention express the double stranded RNA encoded by the DNA construct of the present invention, specifically the col-5 stem-loop RNA. The expression may be monitored by methods known to a person skilled in the art, for example by isolating RNA for the transgenic plant leave and testing for the presence of the stem-loop RNA by employing specific primers in a polymerase chain reaction (PCR).

The present invention also relates to a plant cell or other plant part transformed with the DNA construct for generating siRNA disclosed by the present invention.

Furthermore, also encompassed by the present invention is a plant seed transformed with DNA construct for generating siRNA of the present invention.

The obtained transgenic plant can be used in a conventional breeding scheme to produce more transgenic plants with the same characteristics or to introduce the expression cassette in other varieties of the same or related plant species, or in hybrid plants. Seeds obtained from the transgenic plants contain the expression cassette as a stable genomic insert. Also encompassed by the present invention are transgenic progeny of the transgenic plants described herein. Progeny transgenic plants are grown from seeds of the transgenic plants described herein.

According to yet another aspect, the present invention provides a method for enhancing the production of siRNAs within a plan cell, the method being useful when the parasite target gene is not a plant endogenous gene, said method leading to enhanced resistance of the plant to the parasite. The enhanced production of siRNAs is achieved by transforming a plant that already expresses the double stranded RNA according to the present invention with additional DNA construct comprising a plant expressible promoter operably linked to a fragment of the parasite target gene. The present invention shows for the first time that such co-transformation results in significant amplification of the siRNAs within the plant cell. The siRNAs generated from the double stranded stem loop RNA serve as primers that recognize the mRNA of the introduced fragment of the parasite gene, promoting the formation of additional dsRNAs thus amplifying the production of siRNAs.

According to one embodiment, the present invention provide a method for enhancing the production of siRNAs comprising:
  (a) providing a plant expressing a first DNA construct for generating siRNAs comprising the expression cassette according to the present invention;
  (b) transforming said plant with a second DNA construct, the second DNA construct comprising:
    i. a plant expressible promoter; operably linked to
    ii. a sense nucleotide sequence of about 50-2000 nucleotides derived from the gene of the plant parasite comprising at least 20 contiguous nucleotides having at least 90% identity to the first nucleotide sequence of the expression cassette according to (a); and optionally
    iii. a transcription termination signal.

According to one embodiment, the sense nucleotide sequence derived from the gene of the plant parasite is of 50-2,000 nucleotides in length, preferably 100-500 nucleotides in length.

According to another embodiment, the sense nucleotide sequence derived from the gene of the plant parasite comprises at least 20 contiguous nucleotides having at least 95% preferably 100% identity to the first nucleotide sequence of the expression cassette according to the present invention.

The higher amounts of siRNA in the cytoplasm enhance silencing of the parasite target gene, thus provide better protection of the plant from the parasite. Moreover, Grafts Mountain on plants obtained by this method also exhibits parasite resistance.

According to one embodiment, the transgenic plants are resistant to a parasite selected from the group consisting of plant parasite nematodes, insects and fungi, specifically those consuming plant cytoplasm during their normal life cycle. According to another embodiment, the transgenic plants are resistant to an insect selected from the group consisting of *Hemiptera*, including whiteflies and an aphids, and Acari, including mites and ticks. According to one currently preferred embodiment the transgenic plant is resistant to the nematode *M. javanica*. According to another currently preferred embodiment, the plant is resistant to the insect *B. tabaci*. The normal life cycle of these parasites includes feeding on the plant cytoplasm. The present invention shows for the first time that siRNAs expressed in the plant cell silence the expression of the corresponding parasite gene.

According to one embodiment, the present invention provides a method for producing a nematode-resistant plant, the method comprising transforming a plant with an expression cassette comprising 35S promoter operably linked to a first nucleotide sequence comprising a fragment of the sense nucleotide sequence of *M. Javanica* col-5 gene, and to a second nucleotide sequence comprising a fragment complementary of the sense nucleotide sequence of the col-5 gene, said first and second nucleotide sequences are constructed to flank a spacer sequence derived from an intron of cca1 gene of *A. thaliana* to form a hpRNA structure, upstream to a NOS terminator, such as to produce a transgenic plant comprising the expression cassette of the invention integrated into the genome of the cells of the plant, and selecting a transgenic plant resistant to nematodes, and optionally further comprising selfing or crossing the selected transgenic resistant plant to another plant to obtain progeny plants comprising the construct of the invention integrated into their genomes.

According to one embodiment, the transgenic plants obtained by the methods of the present invention are resistant to the nematode of the species *Meloidogyne*. According to one currently preferred embodiment, the transgenic plants obtained by the methods of the present invention are resistant to the nematode *Meloidogyne javanica*.

According to one currently preferred embodiment, the nematode-resistant transgenic plant comprises the expression cassette according to the present invention, wherein the first nucleotide sequence having the nucleotide sequence set forth in SEQ ID NO:4 and the second nucleotide having the nucleotide sequence complement to the sequence set forth in SEQ ID NO:4, separated by a spacer having the nucleotide sequence set forth in SEQ ID NO:6.

Root nematode affect variety of crops. Nematode infection became a major agricultural problem after the use of methyl bromide for soil disinfestations was forbidden, and the damage caused is estimated in the billion of dollars range (Sasser, J. N. and Freckman, D. W. 1987). The life cycle of the root nematode *M. javanica* is composed of mobile-non-feeding stages, and from sedentary stages that complete the nematode's development inside the roots of their host. The duration of each cycle is around 21 days. The active phase of the nematode begins with hatching of second-stage juveniles (J2) from eggs in the soil, which then invade into the root tissues. Within the roots, females remain sedentary, and their development is mainly characterized by a large increase in body weight due to extensive growth of ovaries and the associated production of eggs. Eggs are released from the females into the soil and J2 worms hatches from the dormant egg. The hatched nematodes migrate to the zone of vascular tissue where feeding is initiated. The established infection of J2 modifies the plant cell, causing progressive wall loss and merging of cytoplasm to form the gall. The J3 females remain sedentary and grow rapidly to reach J4. It is the feeding of the female that causes much of the crop loss associated with these major pests.

Collagen is a major component of nematode's cuticle, and as such was thoroughly studies in the nematode *Caenorhabditis elegans*. The cuticle layers are formed of fibrils that are assembled from tight triple helix, composed of collagen monomers. There are about 100 members of the cuticle collagen genes in *C. elegans*, and the structural changes in the nematode cuticle are suggested to be regulated by differential expression of stage-specific collagen genes: the cuticle of *C. elegans* is synthesized five times during its development and is shed at each molt. Mutations in the collagen genes can alter its shape, and RNAi against collagen genes elicits embryonic lethality. Several collagen genes were isolated from *M. incognita* and several from *M. javanica*, but their specific role in construction the cuticle is currently unknown.

Therefore, as the root nematodes molt three times at the J2 stage when they turn into the sedentary females, collagen genes meet the criteria of a target gene according to the methods of the present invention: it is an integral, specific and essential gene involved in the early stage pf the nematode development in the plant, but it is not an endogenous plant gene.

*M. javanica* was searched for collagen genes that were also shown to be silenced and cause embryonic lethality in RMAi assays. The special collagen gene col-5 was identified. It encodes for a protein of 345 amino acids long which is related to the col-6 gene of *C. elegans*. Examining the phenotype of col-6 silencing in the *C. elegans* wormbase indicated that such silencing result in embryonic lethality after hatching. The col-5 gene shares 66% identity with the col-6 of *C. elegans*. However, it carries an extension of 12 amino acids and additional tyrosine residue in its C-terminus (Liu, J. et al., 2001). col-5 transcript was detected in a mixture of embryonated eggs and also, for a lower extent, in juveniles and young females (Liu, J. et al., 2001). Based on the information obtained in RNAi assays for *C. elegans* col-6, a region within the *M. javaniva* col-5 gene, coding for a fragment of about 540 nucleotides was chosen as a target for silencing. The sense and antisense nucleotides sequences were constructed to flank a spacer comprising an intron sequence derived from the cca1 gene, as the inventors of the present invention has previously shown that this intron sequence enhances silencing when present in an RNAi construct.

According to another embodiment, the present invention provides a method for producing a *Hemiptera*-resistant plant, the method comprising transforming a plant with an expression cassette comprising 35S promoter operably linked to a first nucleotide sequence comprising a fragment of the sense nucleotide sequence of *B. tabaci* vgsc gene, and to a second nucleotide sequence comprising a fragment complementary of the sense nucleotide sequence of the vgsc gene, said first and second nucleotide sequences are constructed to flank a spacer sequence derived from an intron of cca1 gene of *A. thaliana* to form a hpRNA structure, upstream to a NOS terminator, such as to produce a transgenic plant comprising the expression cassette of the invention integrated into the genome of the cells of the plant, and selecting a transgenic plant resistant to nematodes, and optionally further comprising selfing or crossing the selected transgenic resistant plant to another plant to obtain progeny plants comprising the construct of the invention integrated into their genomes.

According to another embodiment, the *Hemiptera*-resistant transgenic plant comprises the expression cassette of the present invention wherein the first and the second nucleotide sequences are a sense nucleotide sequence set forth in SEQ ID NO:1 and fragments thereof and an antisense sequence complement to the nucleotide sequence set forth in SEQ ID NO:1 and fragments thereof, respectively.

According to another embodiment, the present invention provides a method for producing a *Hemiptera*-resistant plant, the method comprising transforming a plant with an expression cassette comprising 35S promoter operably linked to a first nucleotide sequence comprising a fragment of the sense nucleotide sequence of *B. tabaci* eIF5A gene, and to a second nucleotide sequence comprising a fragment complementary of the sense nucleotide sequence of the eIF5A gene, said first and second nucleotide sequences are constructed to flank a spacer sequence derived from an intron of cca1 gene of *A. thaliana* to form a hpRNA structure, upstream to a NOS terminator, such as to produce a transgenic plant comprising the expression cassette of the invention integrated into the genome of the cells of the plant, and selecting a transgenic plant resistant to nematodes, and optionally further comprising selfing or crossing the selected transgenic resistant plant to another plant to obtain progeny plants comprising the construct of the invention integrated into their genomes.

According to another embodiment, the *Hemiptera*-resistant transgenic plant comprises the expression cassette of the present invention wherein the first and the second nucleotide sequences are a sense nucleotide sequence set forth in SEQ ID NO:2 and fragments thereof and an antisense sequence complement to the nucleotide sequence set forth in SEQ ID NO:2 and fragments thereof, respectively.

According to yet another embodiment, the spacer sequence comprises a fragment of the cca1 gene, wherein the nucleotide sequence of the fragment is set forth in SEQ ID NO:6.

According to one currently preferred embodiment, the transgenic plants obtained by the methods of the present invention are resistant to the whitefly *Bemisia tabaci*.

Whiteflies are responsible to direct crop damage resulting from their feeding on the plant phloem, which remove plant sap, interrupt plant tissue and reduce plant vigor. Establishment of dense populations may cause plants death. Whiteflies also excrete honeydew, which promotes sooty mold that interferes with photosynthesis and may lower harvest quality. In cotton, the sugars excreted during whitefly feeding make the cotton fibers sticky and can promote growth of sooty mold, both of which reduce quality. In some hosts, damage can result from whitefly feeding toxins that cause plant disorders such as silver leaf of squash and irregular ripening of tomato. Plant viruses also can be transmitted by whiteflies, such as the geminiviruses in tomatoes, peppers and cabbage, and certain clostroviruses like lettuce infectious yellows in lettuce and melons. Plant disorders and virus transmission are of particular concern because they can occur even when a whitefly population is small. In general, the older the plant when infected with virus or the later the onset of plant disorders, the less damage to the crop, so preventative action is critical. Prevention is also crucial in managing whiteflies in highly cosmetic crops such as ornamental plants, where even low numbers of whiteflies can affect marketability. The whitefly *Bemisia tabaci* is an effective vector of over 60 viruses from several groups, particularly geminiviruses. Many of these have been reported to cause economic damage to a large number of crops. B. tabaci is increasing its worldwide distribution, thus enabling some viruses to infest plant species previously unaffected by whitefly transmitted viruses. B. tabaci also causes damage to the host plant by direct feeding, causing symptoms such as leaf silvering of cucurbits, irregular ripening of tomatoes and leaf yellowing of various hosts. The immature stages excrete honeydew, which makes the plants sticky and susceptible to colonization by sooty moulds.

Two strategies were employed in order to define genes which their silencing would be lethal to B. tabaci.

One approach was to search for known sequences using available databases such as GenBank. Only few genes of B. tabaci have been isolated and sequenced. One of them, found in the GenBank under Accession No. AJ440728 is a partial mRNA for voltage-gated sodium channel. The voltage-gated sodium channel is an essential component in insect cells. As such, it serves as the primary target site of insecticides, specifically pyrethroid insecticides. The gene can be therefore used as a target gene for silencing, as it is essential for the development of various insects, including B. tabaci.

The other approach targeted at isolating genes homologous to known isolated genes which were found to be essential for the development of insects. One of such genes is the eukaryotic translation initiation factor 5A, (eIF5A) which is essential for completion of the life cycle of most eukaryotes including Drosophila. As described in the example section herein below, the isolation and cloning of eIF5A gene of B. tabaci is disclosed in the present invention for the first time. The strategy for cloning the gene from B. tabaci was to use a conserved region of the gene and isolate the corresponding B. tabaci cDNA by RNA Ligase Mediated Rapid Amplification of cDNA Ends (RLM-RACE), using PCR. A fragment of eIF5A gene of B. tabaci was identified and isolated. It encodes for 314 nucleotides, and its deduced amino acid sequence was found to be related to the eIF5A gene of Drosophila yakuba. This fragment was used for the construction of the DNA construct encoding siRNA according to the present invention. A construct containing either the vgsc or eIF5A genes was designed in a form of a stem loop as describes for the col-5 gene herein above.

According to one currently preferred embodiment the DNA construct is introduced into a binaric vector.

The method by which transforming a plant with the construct of the present invention takes place has little importance for obtaining transgenic resistant plants according to the present invention. As described herein above, various methods, including but not limited to Agrobacterium-mediated transformation, microprojectile bombardment, electroporation of compact embryogenic cali, and other methods as known to a person skilled in the art may be used.

According to one currently preferred embodiment Agrobacterium-mediated transformation is used.

The methods of the present invention may be employed to confer parasite resistance to any plant which is susceptible to cytoplasm feeding parasite. Non limiting examples include soybean, wheat, oats, sorghum, cotton, tomato, potato, tobacco, pepper, rice, corn, barley, Brassica, Arabidopsis, sunflower, poplar, pineapple, banana, turf grass, and pine. According to one currently preferred embodiment, the transgenic parasite-resistant plant is tobacco plant. According to another currently preferred embodiment, the transgenic parasite-resistant plant is banana plant.

The obtained transformed plant can be used in a conventional breeding scheme to produce more transformed plants with the same characteristics or to introduce the expression cassette of the invention in other varieties of the same or related plant species, or in hybrid plants. Seeds, fruits, roots, and other organs or isolated organs thereof obtained from the transformed plants contain the chimeric genes of the invention as a stable genomic insert are also encompassed by the present invention.

According to one embodiment, the present invention provides a method of producing a population of transgenic parasite-resistant plant, comprising introducing into at least one cell of a plant a DNA construct for generating siRNAs targeted to a gene of a plant parasite thereby producing a transgenic plant resistant to the development of the parasite in or on the plant; and selfing the transgenic plant or crossing the transgenic plant to another plant to obtain progeny comprising at least one cell transformed with the DNA construct.

According to another aspect the present invention provides plants, as well as their seeds, fruits, roots and other organs or isolated parts thereof, which are parasite-resistant. The expression cassette according to the present invention is integrated and expressed by the genome of the plants, resulting in the inability of the parasite to establish and propagate in or on the plant.

According to one embodiment the present invention provides plants and plant lines comprising the construct of the invention stably integrated into the genome of the cells of the plant, wherein said plants are resistant to parasite development.

According to one embodiment, the parasite is selected from the group consisting of cytoplasm feeding nematodes, insects and fungi. According to one embodiment, the plants are resistant to nematodes. According to one currently preferred embodiment, the nematode is M. javanica. According to another embodiment, the plants are resistant to insects selected from the group consisting of Hemiptera, including whiteflies and an aphids, and Acari, including mites and ticks. According to one currently preferred embodiment, the insect is the whitefly B. tabaci.

The following non-limiting Examples describe the construction of nucleotide molecule for obtaining nematode-resistant plant lines. Unless stated otherwise in the Examples, all recombinant DNA and RNA techniques are carried out according to standard protocols as known to a person with an ordinary skill in the art.

EXAMPLES

Materials and Methods

Oligonucleotides:

The oligonucleotide primers used are detailed in table 1 below.

Endonuclease restriction sites and T7 polymerase recognition sites are designated by italics.

TABLE I

Primers used in the invention

| Primer | Sequence (5' to 3') | Gene (position, bp) | SEQ ID NO. |
|---|---|---|---|
| P1 | IGCRTGICCRTGYTTICCIGTYTT | eIF5A | 7 |
| P2 | GGIAARCAYGGICAYGCIAAR | eIF5A | 8 |
| P3 | CCGGGCTCGAGGCCAAATCCTGGCCAACTTTG | vgsc | 9 |
| P4 | CCGGGATCGATTTTGTTTGTTTCGTTGTCAGCTG | vgsc | 10 |
| P5 | CCGGGCTGCAGTTTGTTTGTTTCGTTGTCAGCTG | vgsc | 11 |
| P6 | CCGGGTCTAGAGCCAAATCCTGGCCAACTTTG | vgsc | 12 |
| P7 | CCGGGAA*GCTT*GCATCCTGAGGTGATTTTCATG | cca1 (3273-3294) | 13 |
| P8 | CCGGG*CTGCAG*CATTGGCCATCTATAAACGAAG | cca1 (33793358) | 14 |
| P9 | CCGGG*CTCGAG*TGTTGTACTTGCCATCAAGGACC | col-5 (704-726) | 15 |
| P10 | CCGGGAA*GCTT*ATATCCGGGAGGAGTACGCGGTTC | col-5 (1521-1498) | 16 |
| P11 | CCGGG*CTGCAG*ATATCCGGGAGGAGTACGCGGTTC | col-5 (1521-1498) | 17 |
| P12 | CCGGG*TCTAGA*TGTTGTACTTGCCATCAAGGACC | col-5 (704-726) | 18 |
| P13 | GTTATGTACAGTCTTTCCAAAGCC | col-5 (245-268) | 19 |
| P14 | GGTTATTGGCCACGTCGATTCTG | ef1-a (33-55) | 20 |
| P15 | GTACTTGATGAAGTCACGAAGTC | ef1-a (303-381) | 21 |
| P16 | *TTAATACGACTCACTATAGGG*AGACCCTGTTCACCAGGAACTCCG | col-5 (954-934) | 22 |
| P17 | CCCGACGTCATGGCCAACACTTGTCAC | gfp (251-268) | 23 |
| P18 | TAATACGACTCACTATAGGGAGACCACTCCTGTTGACGAGGGTGT | gfp (450-432) | 24 |

Growing Nematodes

*M. Javanica* worms were propagated on tomatoes (*Lycopersicon esculetum*) in a temperature-controlled greenhouse. Inoculum of *M. javanica* was prepared by the sodium hypochlorite method of Hussey and Barker (Plant disease reporter 57:1025-1028, 1973). A water suspension of approximately 10,000 infective second-stage juveniles (J2) per plant was pipetted into the soil around the plant roots. After inoculation, plants were maintained at 25° C.

Nematode Staining

Root sections infected with nematodes were subjected to acid-fuchsin staining to visualize the nematodes. Staining was performed by soaking root samples in a 2% water-clorox solution for 4 min, followed by washing the samples with tap water and boiling the roots in 0.35% acid fuchsin (W/V) in 25% acetic acid (V/V). The boiled root samples were washed and kept in acidified glycerol. The stained nematodes within the root samples were visualized by microscopy (×10 magnification).

Growing Whiteflies

Whiteflies were grown on living plant under controlled temperature conditions. Specifically, *B. tabaci* was propagated on cotton plants having 6-8 leave planted in containers having diameter of 15 cm. The containers were placed in greenhouse as to keep the temperature in a range of 25° C. to 30° C., and were covered by a net to keep the whitefly adjacent to the plants. Inoculums of about 50-100 adult whiteflies per plant provide 2,000-5,000 new adult whiteflies after about 35 days.

Plant Transformation

*Nicotiana tabacum* var. *Samsoon* NN seeds were surfaced-sterilized and germinated on MS basal medium (see below). Leaf explants were co-cultivated for 48 hr with overnight culture of *Agrobacterium tumefaciens* EHA105 or LBA 4404 strain containing the desired DNA construct in LB medium containing 100 μg/ml kanamycin and 20 μg/ml acetosyringone. The explants were transferred to regeneration medium (RM) (MS medium+2% sucrose supplemented with 3 μg/ml kinetin, 0.3 6-benzyl amino purine, 250 μg/ml cefotaxime, 25

µg/ml vancomycin and 50 µg/ml kanamycin. Shoots were excised and transferred to elongation medium (EM) (MS+2% sucrose containing 2 µg/ml kinetin and 0.8 µg/ml indole-3-acetic acid (IAA) and antibiotics for selection as in RM).

Elongated shoots were rooted on MS medium containing 0.4 IAA, cefotaxime, 25 µg/ml vancomycin and 200 µg/ml kanamycin. All transgenic plants were maintained in the growth chamber at 25° C. with 16 hr photoperiod.

Example 1

Selecting B. tabaci Genes to be Silenced by siRNA Production in Plants eIF5A Gene As used herein, the terms "gene encoding eukaryotic translation initiation factor 5A (eIF5A) or "eIF5A gene" refer to the B. tabaci eIF5A gene cloned as described in the present invention herein below, comprising SEQ ID NO:2. These terms encompass the full-length sequence of the gene and fragments thereof and include DNA, cDNA, and RNA (e.g., mRNA) sequences.

The gene is an essential gene for completion of the life cycle of most Eukaryotes, including, for example, Drosophila. This gene was chosen for plant-mediated gene silencing in plant insects feeding on the cytoplasm during their normal life cycle, specifically the tobacco whitefly Bemisia tabaci. The B. tabaci gene was isolated and cloned for the first time by the present invention. The strategy for cloning the gene from B. tabaci was to use a conserved region of the gene as is known for other species and isolate the full cDNA by RACE-PCR. A commercial kit of RACE-PCR was used (RNA Ligase Mediated Rapid Amplification of cDNA Ends—RLM-RACE).

Isolation of Total RNA from B. tabaci

Total RNA from Bemisia tabaci was extracted as follows: frozen tissue was ground with liquid nitrogen, mixed with 300 µl TRI Reagent (MRC-USA) and incubated for 5 minutes at room temperature. The homogenate was transferred to a pre-spinned Phase Lock Gel-Heavy tube (Eppenddorf) and 60 µl chloroform were added. The tube was shaken for 15 seconds and subsequently centrifuged at 12,000×g for 10 minutes at 4° C. The upper phase was transferred to a clean tube and 0.8 volume iso-propanol was added. The content of tube was mixed well and left to precipitate overnight at −20° C. The next day the tube was centrifuged at 14,000×g for 30 minutes at 4° C., the pellet washed with 500 µl 75% ethanol and centrifuged for an additional 10 minutes at 12,000×g. Supernatant was removed; the pellet was dried for 2 minutes and re-suspended in 20 µl of RNase-free water pre-heated to 65° C. Following centrifugation, to remove insoluble components, RNA was treated with DNase to eliminate DNA contamination.

PCR Primers Design for RLM-PCR

The strategy employed for primer designing was to find a consensus protein sequence in the available eIF5A protein sequences of various organisms. After such consensus sequences were found degenerated primers were designed. The primers sequences and the consensus sequences of the gene product on which they are based are described below below:

For the forward direction: TGKHGHA, the following degenerate primer P1 was designed:

```
NGCRTGNCCRTGYTTNCCNGTYTT    (SEQ ID NO:7)
```

For the reverse direction: GKHGHAK, the following degenerate primer P2 was designed:

```
GGNAARCAYGGNCAYGCNAAR       (SEQ ID NO:8)
```

"N" represents inosine, "R" represents (A or G), and "Y" represents (C or T)

Cloning of the B. tabaci eIF5A

RLM-RACE was performed according to the instructions provided by the manufacturer in the manual of the FirstChoise™ RLM-RACE kit (Ambion, catalogue No. 1700). The only change from the recommended procedure was the PCR annealing temperature, which was set at 55° C. Two fragments resulted from the above-described RACE-PCR for both directions were isolated and cloned into the pGEM-T easy vector (Promega, USA). Plasmids were isolated and treated with EcoRI and subsequently separated on 1% agarose (FIG. 5A). The fragments were isolated and sequenced, and the derived protein sequence was shown to be homologous to the eIF5A protein of D. yakuba (FIG. 5B). One of the isolated B. tabaci clones, having the nucleotide sequence set forth in SEQ ID NO:2 (FIG. 2) was used for generating the hpRNA as described below.

vgsc Gene

As used herein, the terms "gene encoding voltage-gated sodium channel" or "vgsc gene" refer to the Bemisia tabaci partial mRNA for voltage-gated sodium channel para protein (para gene), strain GRB, Accession number AJ440728, as well as to sequence provided as SEQ ID NO:1. These terms also encompass the full-length sequence of the gene and fragments thereof, and include DNA and cDNA sequences.

A search for genes already isolated from B. tabaci was conducted using the sequences available at the GenBank database. A partial mRNA for voltage-gated sodium channel EST information was found (Accession No. AJ440728). As the product of this gene is essential for the whitefly development, it was decided to silence this gene. The cDNA was amplified using the following oligomers:

```
Primer P3:
                                    (SEQ ID NO:9)
5'-CCGGGCTCGAGGCCAAATCCTGGCCAACTTTG-3'

Primer P4:
                                   (SEQ ID NO:10)
5'-CCGGGATCGATTTTGTTTGTTTCGTTGTCAGCTG-3'

Primer P5:
                                   (SEQ ID NO:11)
5'-CCGGGCTGCAGTTTGTTTGTTTCGTTGTCAGCTG-3'

Primer P6:
                                   (SEQ ID NO:12)
5'-CCGGGTCTAGAGCCAAATCCTGGCCAACTTTG
```

Example 2

RNA Preparation, cDNA Synthesis and Generating the hpRNA Construct for B. Tabaci Genes eIF5A Gene A 314 bp fragment of the isolated eIF5A gene (SEQ ID NO:2) was taken for construction of the RNAi silencing element in a binary vector, using the same techniques and vectors as for DNA construct designed to silence the col-5 gene as described below.

vgsc Gene

Total RNA from *B. Tabaci* was isolated as described herein above. 5 μg of total RNA was used for cDNA synthesis using the Reverse Transcription System kit (Promega). The cDNA was amplified by PCR using primers P3-P6 described above. The sequence of the PCR product was determined and was found to be encoding for the expected sodium channel. The DNA construct for gene silencing according to the present invention is composed of a fragment of the target parasite gene in a sense and antisense orientation, separated by a nucleotide sequence derived from an intron of cca-1 gene, wherein the intron is forming a loop. The Primers P7 and P8 (table 1 herein above) were used to amplify the cca-1 intron (107 nucleotides), which was cloned into the Hind III-PstI sites of pBluescript. To generate the hpRNA construct, the 420 bp PCR product of vgsc gene (positions 1-420) was cloned between (XhoI-ClaI) upstream to the cca-1 intron, and the same fragment in the anti-sense orientation was cloned between (PstI-XbaI). The entire 940 bp long sequence was cloned into the binary vector pBIN(117) downstream to the 35S promoter (XhoI-XbaI/SpeI).

Example 3

Selecting a *M. javanica* Gene to be Silenced by siRNA Production in Plants

Gene Selection

Silencing of nematode genes required for early developmental stage should result in lethality and stop the propagation of the nematode within the roots. Thus, a search was conducted for genes that were identified in *M. javanica*, were shown to cause early stage lethality and were also demonstrated to be silenced in RNAi assay in *C. elegans* (http://www.wormbase.org/db/serches/blast; Gonczy, P. et al., 2000; Frazer, G. A. et al., 2000). Two genes were identified and chosen for further analysis. Calponin, which is a troponin-like molecule linked to actin/tropomyosin filaments (Takahashi, K. et al., 1991; Castagnone-Sereno P. et al, 2001), and a special collagen gene, col-5 (Liu, J. et al., 2001). Two additional genes, hsp90 and the elongation factor 1 alpha (ef1-α), were excluded as they also exist in plants and their silencing might have deleterious effects on the host. col-5 gene was selected as a candidate for silencing as collagen is the major component of the nematode cuticle. The col-5 transcript is present mainly in embryonated eggs and also in the transition to form the J2 juvenile nematode.

As used herein, the term "*M. javanica* collagen gene" or "col-5", refers to the full-length col-5 gene of *M. javanica*, Accession number AF289026, further defined by the nucleotide sequence set forth in SEQ ID NO:3. These terms also encompass fragments of the col-5 sequences and include DNA, cDNA, and RNA (e.g., mRNA) sequences.

RNA Preparation, cDNA Synthesis and Generating the hpRNA Construct

*Meloidogyne javanica* total RNA was purified using Tri Reagent (Sigma), according to the manufacturer protocol. 5 μg of total RNA was used for cDNA synthesis using the Reverse Transcription System kit (Promega), followed by PCR amplification using TaKaRa DNA polymerase (Biological industries) to produce the fragments to generate hpRNA construct. The construct carries sense and antisense information and the loop is composed of the cca-1 intron. The Primers P7 and P8 used to amplify the cca-1 intron (107 nucleotides), which was cloned into the Hind III-PstI sites of pBluescript. The stem of the hpRNA was constructed in two steps. First, primers P9 and P10 were used to amplify partial sense information of the col-5 gene from the cDNA, and to clone it into XhoI-HindIII sites of the vector. Second, primers P11 and P12 were used to amplify the antisense fragment, which was cloned at the PstI and XbaI sites of the same vector. As the col-5 gene fragment of positions 704-1521 comprises few introns (GenBank gi: 15077110, Accession number AF289026), the amplified cDNA fragment of the stem in the col-5 construct was of 543 nucleotides. The entire hpRNA construct was removed by XhoI and XbaI digestion, and ligated into the XhoI-SpeI sites of the binary vector pBIN (117), downstream from a CaMV 35S promoter and upstream a NOS terminator. All cloned PCR products were confirmed by sequencing. NPTII designates the kanamycin-resistant gene; LB and RB indicate the left and right borders of Ti plasmid, respectively. The vector was transformed into *Agrobacterium tumefaciense* EHA105, and the last was used to infect *Nicotiana tabacum* Samson NN leaf-explants to generate transgenic plants.

Example 4

Expression of col-5 hpRNA by Transgenic Plants

Figure 6A:
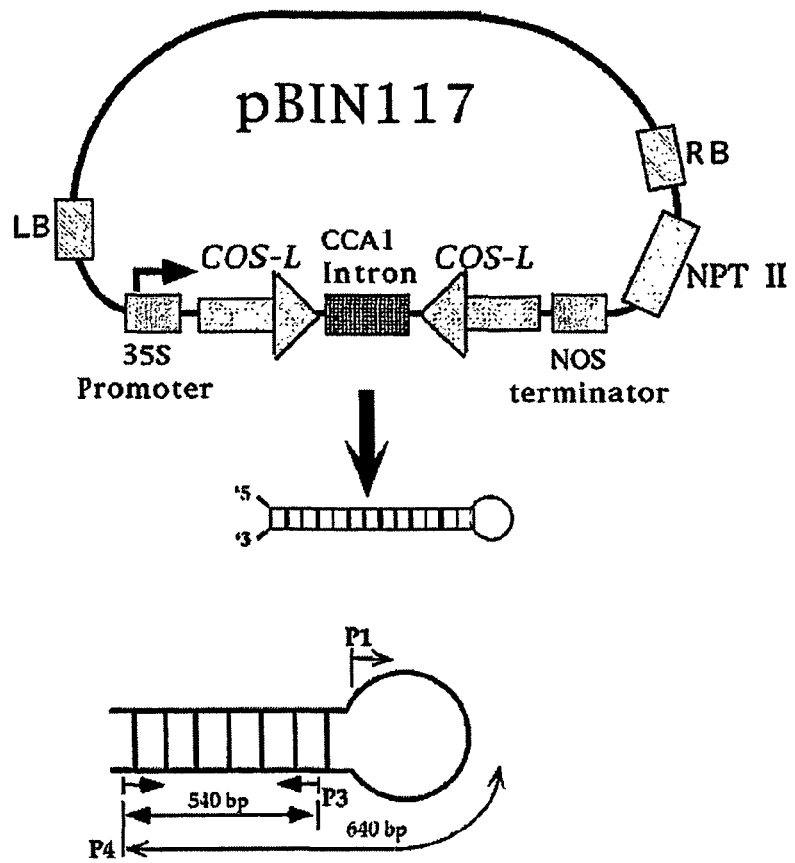
FIG. 6A: The pBIN(117) construct expresses the hpRNA structure for inactivation of *M. javanica* col-5 gene. The small intron of the cca-1 gene is depicted as a loop, and is flanked by two opposite directed fragments of the col-5 gene.

FIG. 6 shows a schematic illustration of the DNA construct comprising the expression cassette comprising the hpRNA. Transgenic *N. tabacum* plants carrying this construct were obtained by *Agrobacterium*-mediated transformation. RT-PCR analysis was performed to examine the expression of the hairpin RNA (hpRNA) derived from the stem-loop construct. Total RNA was purified from leaves using the LiCl method, and treated with DNaseI (Ambion) to remove traces of genomic DNA and cDNA was synthesized using random primers (Promega kit). The cDNA was amplified by gene-specific oligonucleotides. The levels of RT-PCR products were quantified by Southern analysis using randomly labeled col-5 and ef1-α probes (Promega).

Figure 6B:
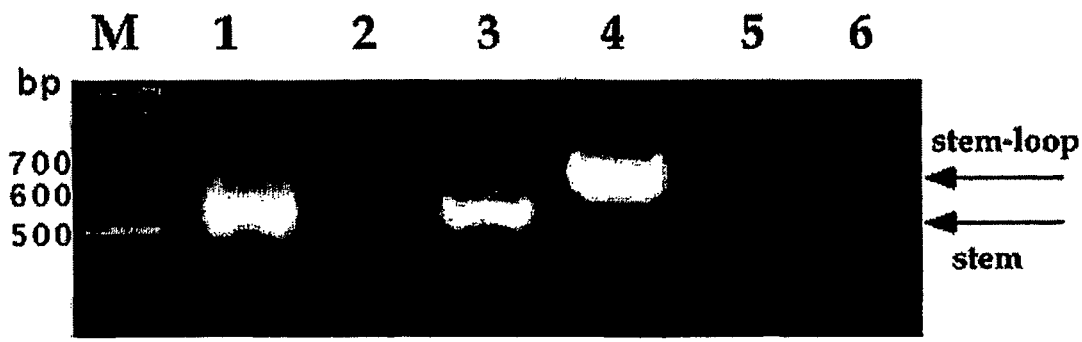
FIG. 6B: RT-PCR analysis of RNA from $T_2$ transgenic plants. Lane 1 and lane 4: stem and stem-loop products obtained using the construct described in A as a template. Lane 2: RT-PCR product of stem specific primers (P9 and P10). lane 3: RT-PCR product with P10 as primer. lane 5: RT-PCR product with primers P7 and P10. lane 6: RT-PCR product with primers P7 and P10. The one Kb DNA Ladder was used as a marker (M) and the size of the fragments is indicated.

The analysis was performed with oligonucleotide matching the stem or the stem-loop sequences, as described and illustrated in FIG. 6B. Only RNA comprising the stem, but not an RNA carrying both stem and loop sequences was detected by RT-PCR, suggesting that the intron was spliced. Similar results from RT-PCR analysis were also obtained from $T_1$ and $T_2$ plants, confirming the stable integration of a single insertion encoding the silencing construct.

Example 5

Resistance of the Transgenic Plants to Nematode Infection

Figure 7:
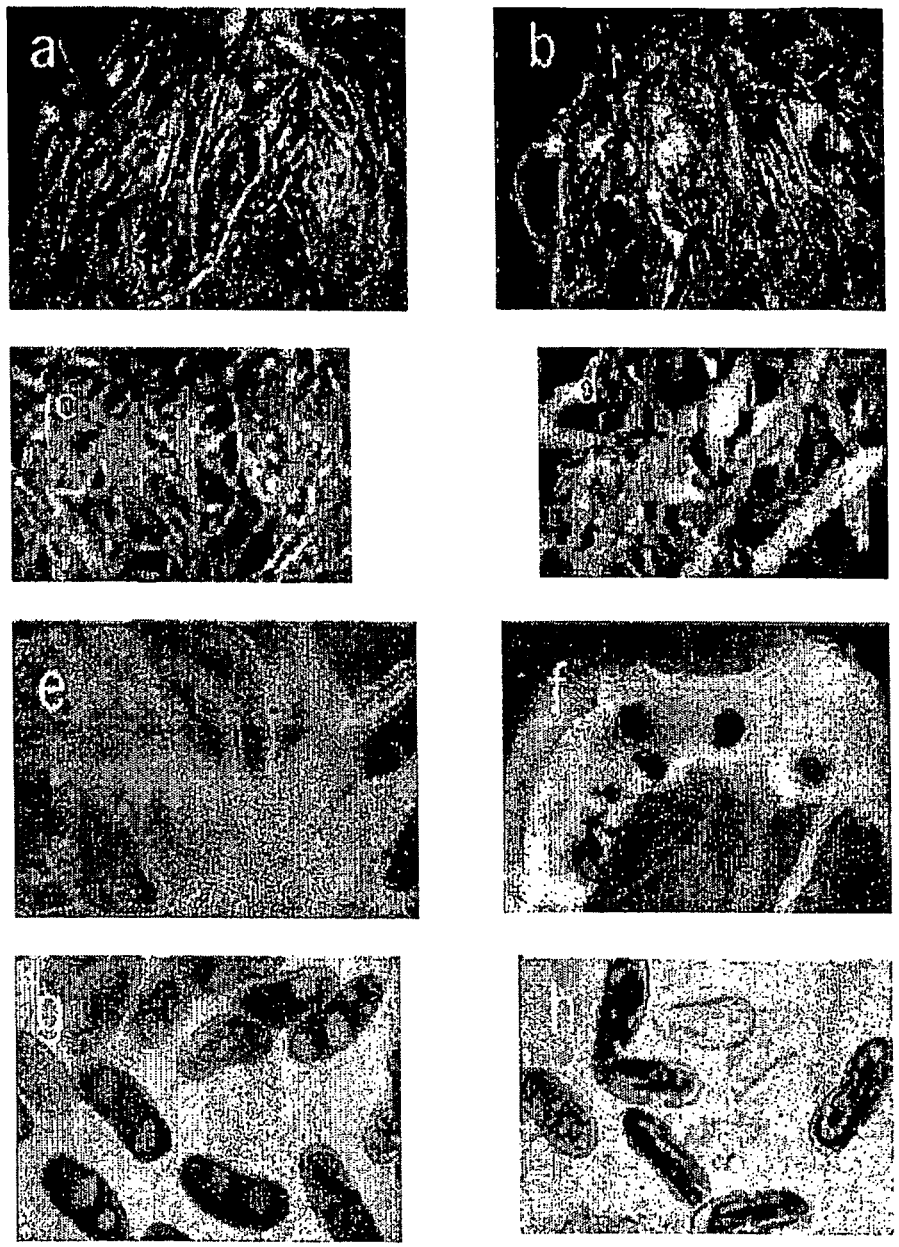
FIG. 7 shows transgenic *Nicotiana tabacum* plants resistant to *M. javanica* infection. Wild type infected roots are presented in panels (b,d,f,h) and roots from the T-37 transgenic plant in panels (a,c,e,g). The pictures in (a,b) and (c,d) depicts primary and secondary infection, respectively. Root sections were subjected to acid-fuchsin staining to visualize the nematodes (e, f). Eggs taken out from stained nematodes were visualized by ×100 magnification, using a light microscope (g,h).

Transgenic plants obtained as above and expressing the col-5 hpRNA examined for their resistance to nematodes. The plants were infected with nematode eggs, 80% of which were at the J2 stage. At seven to eight weeks post-infection, the roots were examined. Whereas large galls were observed in wild-type plants as a result of secondary infection (FIG. 7*a*), only small galls were observed in the transgenic plants and only at the primary sites of infection (FIG. 7*b*). In addition, the mass of roots of transgenic plants was almost normal, and galls were hardly noticed at the newly formed roots, suggesting little or no secondary infection (FIG. 7*d*). In contrast, in the wild type plants the root mass was appreciably smaller and newly formed roots were characterized by the formation of galls (FIG. 7*c*). Indeed, staining roots by acid fuchsin confirmed a dramatic decrease in the number of nematodes within the transgenic roots (FIG. 7*f*) compared with the wild type roots (FIG. 7*e*). The propagation of the nematodes within the infected plants was further analyzed by examining the eggs released from mature female nematodes. Wild type infected plants contained eggs of various embryonic developmental stages including J1, J2 and hatching eggs (FIG. 7g). In contrast, eggs extracted from the transgenic plants were abnormal and formed cynsitium of undifferentiated cells at the center of the egg (FIG. 7h).

Example 6

Resistance of the Plants is Due to Silencing of the Nematodes col-5 Gene

To correlate the resistance to nematode infection with the inability of the nematodes to establish a secondary productive cycle, silencing of the col-5 transcript was examined. Mature J4 nematodes, carrying eggs, from wild type and transgenic $T_2$ plant (Plant #37) were recovered from roots, 7-8 weeks post-infection. RNA extracted from the nematodes was subjected to RT-PCR, and then analyzed by Southern blotting. Specific primers, P13 and P16 (Table 1 herein above) were used to amplify col-5 endogenous transcripts, as primer P13 is situated outside the col-5 sequence used for producing the silencing construct. As a control, to verify that equal amounts of RNA were used, the same cDNA served for amplification of the ef1-α transcript, using primers P14 and P15 (Table 1).

The RT-PCR products obtained were gene-specific and their level was quantitated by hybridization with the specific clones. The results are presented in 8A, demonstrating a significant reduction of almost 100% in the level of the col-5 transcript, with no change in the level of the control transcript, ef1-α.

To attribute the silencing of the nematodes to ingestion of siRNAs produced by the plants, the presence of col-5 siRNAs in the infected plants was examined. RNA was extracted from roots of transgenic and wild type plants infected with nematodes, and from mature J4 nematodes carrying eggs that were collected from the infected roots. RNA isolation from both plant and nematodes was performed as described above. As a control for the size of siRNA, RNA from transgenic plants carrying gfp and hpRNA construct directed to silence this gene (generated using primers P17 and P18) was used. The RNA was subjected to RNase protection assay with antisense probes specific to either col-5 or gfp: total RNA (15 μg) was mixed with 125,000 cpm of gel-purified RNA probe and concentrated by ethanol precipitation. The pellet washed and dissolved in hybridization buffer (40 mM PIPES, pH 6.4, 80% formamide, 0.4 M sodium acetate, 1 mM EDTA). Samples were boiled for 1 minute and incubated at 37° C. for 14-16 hours. After the hybridization, the samples were diluted 1:10 with a solution consisting of 10 mM Tris-HCl (pH 7.5), 5 mM EDTA and 200 mM Sodium acetate containing 2.5 units/ml RNase ONE (Promega). Digestion was performed at 30° C. for 1 hour and terminated by proteinase K digestion. Following phenol-chloroform extraction, the protected products were precipitated with ethanol in the presence of 20 μg glycogen and analyzed on an 8% polyacrylamide-7M urea denaturing gel.

Figure 8A:
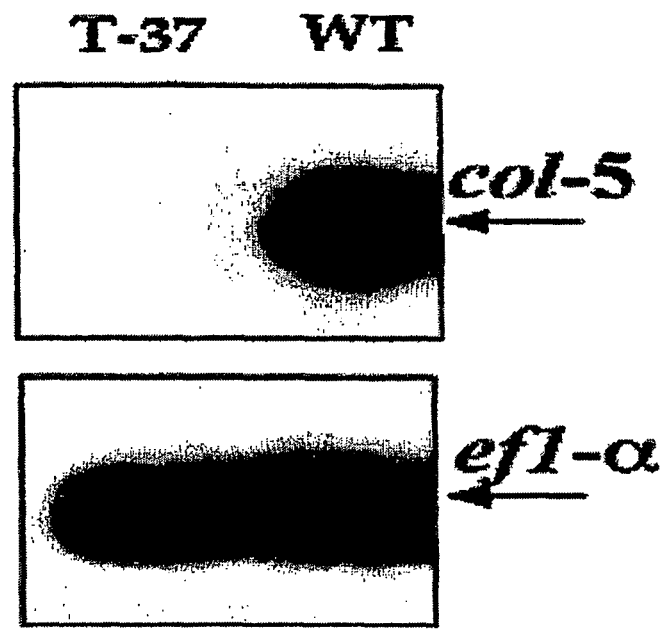
FIG. 8A shows col-5 and efa-1 mRNA level in nematodes grown within wild type and neamtode-resistant transgenic plants.
Figure 8B:
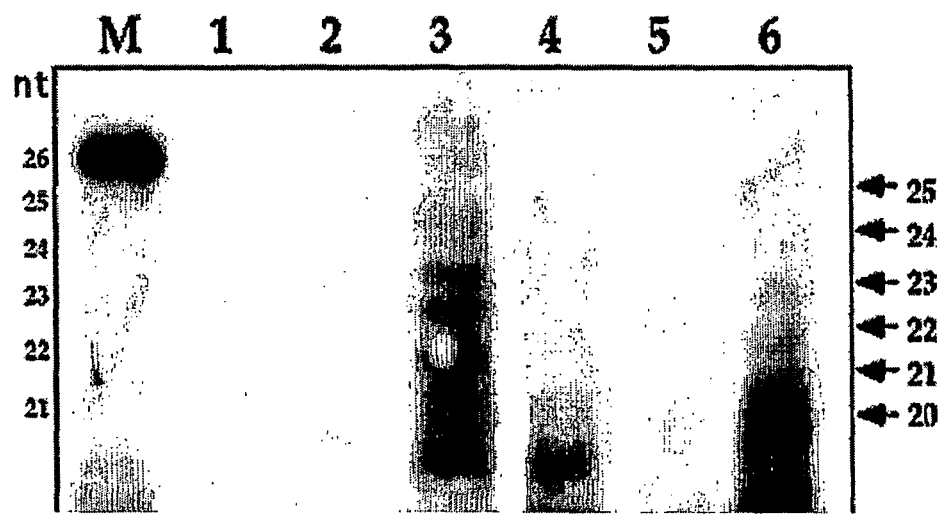
FIG. 8B shows the presence of siRNA related to col-5 in roots of transgenic plants and in nematodes isolated from them. Lane 1 and lane 2: protected fragments obtained from wild-type and GFP transgenic plants, respectively. Lane 3: protected fragments derived from infected root of transgenic plant using a col-5 probe. Lane 4 and lane 5: protected fragments from nematodes rescued from wild type and transgenic plant roots, respectively. pBR322 MspI digest was used as a marker (M), and sizes of fragments differ in one nucleotide is indicated.

The results, presented in FIG. 8B, demonstrate the presence of protected RNA in the range of 21 to 26 nucleotides, typical of siRNAs in plants (FIG. 8B, lane 3). A very similar pattern of siRNA was obtained with RNA extracted from the col-5 transgenic plant roots (#37), using the col-5 probe (FIG. 8B, lane 4). However, in RNA extracted from pure nematodes that were collected from the transgenic plants (#37), a dominant band of 21 nucleotides, which is typical to nematodes siRNA was detected (FIG. 8B, lane 6). This result suggests that siRNAs ingested by the nematode are amplified within the nematode by RNA-dependent RNA polymerase (RdRp).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A transgenic plant comprising at least one cell transformed with a DNA construct for generating siRNAs comprising the Col-5 polynucleotide of *Meloidogyne javanica* gene sequence as set forth in SEQ ID NO:4, wherein the plant is resistant to the development of subsequent generations of the parasite in or on said plant, wherein the DNA construct comprises an expression cassette comprising:
   a) at least one plant expressible promoter operably linked to;
   b) a polynucleotide sequence encoding a double stranded RNA, comprising:
      i) a first nucleotide sequence of at least 20 contiguous nucleotides having at least 90% sequence identity to the sense nucleotide sequence of the sequence set forth in SEQ ID NO:4;
      ii) a second nucleotide sequence of at least 20 contiguous nucleotides having at least 90% sequence identity to the complementary sequence of the sense nucleotide sequence of the sequence set forth in SEQ ID NO:4; and optionally;
      iii) a transcription termination signal.

2. The transgenic plant according to claim 1, wherein the plant parasite is a cytoplasm-feeding nematode.

3. The transgenic plant according to claim 1, wherein the DNA construct further comprises a selectable marker.

4. The transgenic plant according to claim 3, wherein the selectable marker is a polynucleotide sequence encoding a product conferring antibiotic resistance.

5. The transgenic plant according to claim 1, wherein the DNA construct further comprises an expression control sequence selected from the group consisting of an enhancer, a transcription factor, a splicing signal, and a stop codon.

6. The transgenic plant according to claim 1, wherein the expression cassette comprises the first and the second nucleotide sequences operably linked to the same promoter.

7. The transgenic plant according to claim 6, wherein the first and the second nucleotide sequences are separated by a spacer sequence.

8. The transgenic plant according to claim 7, wherein the ratio between the length of the first nucleotide sequence and the length of the spacer sequence is from about 5:1 to about 10:1.

9. The transgenic plant according to claim 1, wherein the expression cassette comprises promoter selected from the group consisting of constitutive promoters, inducible promoters, tissue specific promoters and developmental stage specific promoters.

10. The transgenic plant according to claim 9, wherein the constitutive promoter is selected from the group consisting of the CaMV 35S promoter, the enhanced CaMV 35S promoter, the Figwort Mosaic Virus (FMV) promoter, the mannopine synthase (mas) promoter, the nopaline synthase (nos) promoter and the octopine synthase (ocs) promoter.

11. The transgenic plant according to claim 9, wherein the inducible promoter is selected from the group consisting of pathogenesis related (PR) promoters, heat-shock promoters, a nitrate-inducible promoters, hormone-inducible promoters and light-inducible promoters.

12. The transgenic plant according to claim 9, wherein the tissue specific promoter is selected from the group consisting of root, tuber, vascular tissue, mesophyl tissue, stem, stamen, fruit, seed and leaf specific promoters.

13. The transgenic plant according to claim 12, wherein the tissue specific promoter is a root specific promoter, selected from the group consisting of the promoter of b1-tubulin gene of *Arabidopsis* (TUB-1); the promoter of metallothionein-like gene from *Pisum sativum* (PsMTA); the RPL16A promoter from *Arabidopsis thaliana*; the ARSK1 promoter from *A thaliana*; the promoter of AKT1 gene of *A thaliana*; and the promoter of *Lotus japonicus* LJAS2 gene.

14. The transgenic plant according to claim 12, wherein the tissue specific promoter is leaf-specific promoter selected from the group consisting of rbcs promoter from rice or tomato; the chlorella virus adenine methyltransferase gene promoter; the aldP gene promoter from rice and the potato pin2 promoter.

15. The transgenic plant according to claim 1, wherein the parasite gene Col-5 as set forth in SEQ ID NO:4 and is not an endogenous plant gene.

16. The transgenic plant according to claim 1, wherein the product of the parasite Col-5 as set forth in SEQ ID NO:4 has no significant deleterious effect on the plant cell.

17. The transgenic plant according to claim 1, wherein the parasite gene is associated with early developmental stages of subsequent generations of the parasite in or on the plant.

18. The transgenic plant according to claim 17, wherein the parasite is a nematode.

19. The transgenic plant according to claim 1, selected from the group consisting of soybean, wheat, oats, sorghum, cotton, tomato, potato, tobacco, pepper, rice, corn, barley, *Brassica*, *Arabidopsis*, sunflower, poplar, pineapple, banana, turf grass, and pine.

20. A seed of the transgenic plant according to claim 1, wherein the seed comprises the DNA construct that comprises the DNA construct to identify a product that is not found in nature for generating siRNAs targeted to the Col-5 polynucleotide of *Meloidogyne javanica* gene sequence as set forth in SEQ ID NO:4.

21. A leaf of the transgenic plant according to claim 1.

22. A stem of the transgenic plant according to claim 1.

23. A tissue culture derived from the transgenic plant according to claim 1.

24. A DNA construct comprising an expression cassette comprising:

a) at least one plant expressible promoter operably linked to;

b) a polynucleotide sequence encoding a double stranded RNA, comprising:

i) a first nucleotide sequence of at least 20 contiguous nucleotides having at least 90% sequence identity to the sense nucleotide sequence of the sequence set forth in SEQ ID NO: 4;

ii) a second nucleotide sequence of at least 20 contiguous nucleotides having at least 90% sequence identity to the complementary sequence of the sense sequence of the sequence set forth in SEQ ID NO: 4; and optionally iii) a transcription termination signal.

25. The DNA construct according to claim 24 further comprising a selectable marker.

26. The DNA construct according to claim 25, wherein the selectable marker is a polynucleotide sequence encoding a product conferring antibiotic resistance.

27. The DNA construct according to claim 24, further comprising an expression control sequence selected from the group consisting of an enhancer, a transcription factor, a splicing signal, and a stop codon.

28. The DNA construct according to claim 24, wherein the expression cassette comprises the first and the second nucleotide sequences operably linked to the same promoter.

29. The DNA construct according to claim 28, wherein the first and the second nucleotide sequences are separated by a spacer sequence.

30. The DNA construct according to claim 29, wherein the ratio between the length of the first nucleotide sequence and the length of the spacer sequence is from about 5:1 to about 10:1.

31. The DNA construct according to claim 24, wherein the expression cassette comprises promoter selected from the group consisting of constitutive promoters, inducible promoters, tissue specific promoters and developmental stage specific promoters.

32. The DNA construct according to claim 31, wherein the constitutive promoter is selected from the group consisting of the CaMV 35S promoter, the enhanced CaMV 35S promoter, the Figwort Mosaic Virus (FMV) promoter, the mannopine synthase (mas) promoter, the nopaline synthase (nos) promoter and the octopine synthase (ocs) promoter.

33. The DNA construct according to claim 31, wherein the inducible promoter is selected from the group consisting of pathogenesis related (PR) promoters, heat-shock promoters, a nitrate-inducible promoters, hormone-inducible promoters and light-inducible promoters.

34. The DNA construct according to claim 31, wherein the tissue specific promoter is selected from the group consisting of root, tuber, vascular tissue, mesophyl tissue, stem, stamen, fruit, seed and leaf specific promoters.

35. The DNA construct according to claim 34, wherein the tissue specific promoter is a root specific promoter, selected from the group consisting of the promoter of b1-tubulin gene of *Arabidopsis* (TUB-1); the promoter of metallothionein-like gene from *Pisum sativum* (PsMTA); the RPL16A promoter from *Arabidopsis thaliana*; the ARSK1 promoter from *A thaliana*; the promoter of AKTI gene of *A thaliana*; and the promoter of *Lotus japonicus* LJAS2 gene.

36. The DNA construct according to claim 34, wherein the tissue specific promoter is leaf-specific promoter, selected from the group consisting of rbcs promoter from rice or tomato; the chlorella virus adenine methyltransferase gene promoter; the aldP gene promoter from rice and the potato pin2 promoter.

37. The DNA construct according to claim 24, wherein the parasite gene is not an endogenous plant gene.

38. The vector according to claim 24, wherein the product of the parasite gene has no significant deleterious effect on the plant cell.

39. The DNA construct according to claim 24, wherein the parasite gene is associated with early developmental stages of the parasite in or on the plant.

40. The DNA construct according to claim 39, wherein the parasite is a nematode.

41. The DNA construct according to claim 24, wherein the first nucleotide sequence has at least 95% identity to the sense nucleotide sequence of the sequence set forth in SEQ ID NO: 4.

42. The DNA construct according to claim 24, wherein the second nucleotide sequence has at least 95% identity to the sequence complementary to the sense nucleotide sequence of the sequence set forth in SEQ ID NO: 4.

43. The DNA construct according to claim 24, wherein the first nucleotide sequence comprises a nucleic acid sequence having at least 90% identity to the nucleotide sequence of SEQ ID NO: 4.

44. The DNA construct according to claim 24, wherein the second nucleotide sequence comprises a nucleic acid sequence having at least 90% identity to the complement of the nucleotide sequence of SEQ ID NO: 4.

45. The DNA construct according to claim 29, wherein the spacer sequences comprises a nucleotide sequence derived from an intron.

46. The DNA construct according to claim 29, wherein the spacer comprises a fragment of the nucleotide sequence of *Arabidopsis thaliana* cca-1 gene, said fragment having the nucleotide sequence set forth in SEQ ID NO:6.

47. The DNA construct according to claim 24, wherein the transcription termination signal is NOS terminator.

48. A vector comprising the DNA construct according to claim 24.

49. The vector according to claim 48 suitable for transforming the DNA construct into a plant cell.

50. A host cell characterized in that it comprises the DNA construct according to claim 24.

51. A method for producing the transgenic plant resistant to a parasite according to 1, comprising introducing into at least one cell of a plant the DNA construct for generating siRNAs targeted to the Col-5 polynucleotide of *Meloidogyne javanica* gene sequence as set forth in SEQ ID NO:4 of the plant parasite thereby producing a transgenic plant resistant to the development of the subsequent generation of said parasite in or on the plant.

52. The method for producing a population of transgenic plants resistant to the subsequent generation of a nematode comprising:
 a) selecting a transgenic plant comprising the DNA construct of claim 24, integrated into the genome of at least portion of the plant cells; and
 b) selfing the transgenic plant or crossing the transgenic plant to another plant to obtain progeny comprising the DNA construct integrated into the genome of at least portion of their cells.

53. The method according to claim 52, further comprising the step of challenging the transgenic plants with the nematodes and selecting plants resistant to the subsequent generation of the nematodes.

54. The method according to claim 51, wherein the DNA construct is introduced into at least one cell of the plant by a method selected from the group consisting of *Agrobacterium*-mediated transformation, microprojectile bombardment, pollen mediated transformation, plant RNA virus mediated transformation, liposome mediated transformation, direct gene transfer and electroporation of compact embryogenic calli.

55. The method according to claim 51, wherein the parasite is a cytoplasm-feeding nematode.

56. The method according to claim 55, wherein the parasite is a nematode.

57. The method according to claim 56, wherein the parasite is a nematode of the species *Meloidogyne*.

58. The method according to claim 57, wherein the nematode is *Meloidogyne javanica*.

59. The method according to claim 51, wherein the plant parasite is a nematode and the DNA construct comprises a 35S promoter operably linked to a first polynucleotide sequence having the sequence set forth in SEQ ID NO:4 and to a second polynucleotide sequence complementary to SEQ ID NO:4, said first and second nucleotide sequences are constructed to flank a spacer sequence having the nucleotide sequence set forth in SEQ ID NO: 6 to form a hpRNA structure, upstream to a NOS terminator.

60. A plant generated by the method of claim 51, wherein the plant is resistant to a cytoplasm-feeding parasite.

61. The plant according to claim 60, wherein the cytoplasm-feeding parasite is a nematode.

62. The plant according to claim 61, wherein the parasite is a nematode of the species *Meloidogyne*.

63. The method according to claim 62, wherein the nematode is *Meloidogyne javanica*.

* * * * *

SEQUENCE LISTING

```
<160> NUMBER OF SEQ ID NOS: 26

<210> SEQ ID NO 1
<211> LENGTH: 420
<212> TYPE: DNA
<213> ORGANISM: Bemisia tabaci

<400> SEQUENCE: 1
gccaaatcct ggccaacttt gaatctgttg atttcaatcg tgggccgaac agttggggcc      60
ttaggaaatt tgactttgt tttgtgtatc attattttca tttttgctgt gatgggaatg     120
caactattcg ggaagaatta tacagacaat gttgatcgct ttcctggcgg agaactacct    180
cggtggaatt ttactgactt catgcactca ttcatgatcg tttttcgagt cctctgcgga    240
gaatggattg agtccatgtg ggactgtatg catgttggtg atgtgtcctg tattcctttt    300
tttttagcca ctgtcgttat cggttacctt gtagttttaa atcttttctt agcgttgttg    360
ctgagtaatt tcggatcatc aagcttatcg gcgccaacag ctgacaacga aacaaacaaa    420
```

```
<210> SEQ ID NO 2
<211> LENGTH: 314
<212> TYPE: DNA
<213> ORGANISM: Bemisia tabaci

<400> SEQUENCE: 2
ggaagcacgg gcatgcgaaa gtgcatttgg ttggtcttga tattttctct ggaaagaagt      60
atgaagatat ctgtccatcc actctacaac atggacgttc catttgtaaa gcgtgaagat     120
tatcagttaa cagatatctc cgatgatggc tatctgtgtt tgatgtcaga caatggagat     180
cttcgtgaag acttaaaaat gccagaagga gaattaggtg ttcaactcaa agcagacttc     240
gatagcggag aggagttatt gtgtacagtt ttgaaagctt gtggtgagga gtgtgtaatt     300
gcgatcaaga caaa                                                      314

<210> SEQ ID NO 3
<211> LENGTH: 1633
<212> TYPE: DNA
<213> ORGANISM: Meloidogyne javanica

<400> SEQUENCE: 3
gcgagagggt ctttccattg tccttccgtc cctcgagtac ctttcacgtt gttcctccgc      60
ttaacggcga tatggaacct aaagagcagt tctgccttaa agagacggta ttgactaaaa     120
attttcgaga aaaatgtatt tttaaaggat gagcaccgtc aaatgcgacg aattgctttt     180
attttcgaga aaaatgtatt tttaaaggat gagcaccgtc aaatgcgacg aattgctttt     240
tatagttatg tacagtcttt ccaaagccat ttaattgttg aaattgacca ttgtaaggta     300
aaaaatgaac ttttgatttt gttaaacccc ccttaaattt tttgaactta tcttttgcat     360
tttgatggaa aaaaaagttt gtgaccaagc atgagagatt atattgagaa cagccttact     420
ttatttttca aatgaccttg aattttaga attaaatatt taggcaaaaa gtcgagatat     480
gtggctagaa atgacagcac ttcaaatcgg aaaaggacac gtagaccgag ttaaacgtgg     540
ttggctattt ggccagtggg tacctgaaaa tggttacgaa ccagcacaaa ctggccttc     600 aaatactgtc caatcagcaa tatctcaagg cccaagtggg gcaacctatg gacagggagc     660
tgctggttat caacctgttg ttgctccaaa acccgctcca gtttgttgta cttgccatca     720
aggaccgccc ggacctatcg gtcccgaagg agaacctggg ccagatgggg aggatggacc     780
taatggaaag gatggaacta gtggaaaaga tgcacggatt ttgccagctc ctttggagcc     840
tccttgtatt atatgcccgc caggacctgc tggtcctcaa ggccctgctg gtgctaaagg     900
accacctggc tcgctgggag agccgccaaa agacggagtt cctggtgaac agggaatggt     960
tggacaacat ggtccacccg gtatgtttgt ttacaaataa atttagactc ggatgtgtct    1020
gggtctggcg cggaaactaa tgtaaatata ataattttga tttcaggacg acccggacga    1080
gaaggaccta gaggagcgcc tgtcagttta attaatattt ctctttaatt tctttcatat    1140
tcagggctct cctggtcgtc tcattcccgt gcctggacct caaggtccag ctggacctcc    1200
tggcgttgtt ggaccaccag gagcccctgg agctgccgga ccacctggtc aatcatttga    1260
aggtcctcct ggacctcctg gcgagcctgg acgtcccgga cgtgaaggcc gtcctggcgg    1320
acctgtaagt ttttatttct ctaaacttttt gaagttaatt tatattttta acaattcagg    1380
gacctgctgg acctcctgga caagatggag aaaagggcag ttgtgaacat tgtccaggta    1440 ttttcgaaa atatttttca caattccat taatttttct cttttttgtg ttgtatagaa    1500
ccgcgtactc ctcccggata tttgcgcgag gcaagtgcaa aaagtggtgg atatcattaa    1560
ttattattgt gatattaaac tactactact ttttattctt tcaaacaaaa agaaggaacc    1620
```

<210> SEQ ID NO 4
<211> LENGTH: 818
<212> TYPE: DNA
<213> ORGANISM: Meloidogyne javanica

<400> SEQUENCE: 4

```
tgttgtactt gccatcaagg accgcccgga cctatcggtc ccgaaggaga acctgggcca      60
gatggggagg atggacctaa tggaaaggat ggaactagtg gaaaagatgc acggattttg     120
ccagctcctt tggagcctcc ttgtattata tgcccgccag gacctgctgg tcctcaaggc     180
cctgctggtg ctaaaggacc acctggctcg ctgggagagc cgccaaaaga cggagttcct     240
ggtgaacagg gaatggttgg acaacatggt ccacccggta tgtttgttta caataaaatt     300
tagactcgga tgtgtctggg tctggcgcgg aaactaatgt aaatataata attttgattt     360
caggacgacc cggacgagaa ggacctagag gagcgcctgt cagtttaatt aatatttctc     420
tttaatttct ttcatattca gggctctcct ggtcgtctca ttcccgtgcc tggacctcaa     480
ggtccagctg gacctcctgg cgttgttgga ccaccaggag cccctggagc tgccggacca     540
cctggtcaat catttgaagg tcctcctgga cctcctggcg agcctggacg tcccggacgt     600
gaaggccgtc ctggcggacc tgtaagtttt tatttctcta aacttttgaa gttaatttat     660
attttaaca attcagggac ctgctggacc tcctggacaa gatggagaaa agggcagttg     720
tgaacattgt ccaggtattt ttcgaaaaat attttcacaa attccattaa ttttttctctt    780
ttttgtgttg tatagaaccg cgtactcctc ccggatat                            818
```

<210> SEQ ID NO 5
<211> LENGTH: 5242
<212> TYPE: DNA
<213> ORGANISM: Arabidopsis thaliana

<400> SEQUENCE: 5

```
gagctcctcc ttctcgacta gcctccgcct ccgcctcttc tccgtcgtgc atttcacttc      60
ccacacttcc gattcagtct catacccgtg ccgctaaagc cactgcttac tgttcgtttt     120
ccataaatct gaagattttt cttttcactt ttaatttcga gtttaaagtt tcaaactttc     180
gaaatgggtt ttggtttta ggtcggaaga ttgtgaggaa cgttgtgacg agagctacta     240
ctgaagttgg tgaagctcct gccactacta ccgaagctga gactactgag ttacctgaaa     300
tcgtcaagac tgctcaagaa gctgtaaata ctcttacttt atttatacaa tgatgattct     360
acctcttgct tctgggttac atgtactgaa tttggttgtt tggattgaag tgggagaaag     420
tggatgacaa gacgctattg gttctcttgc ctttgctggt gtagtggctc tttggggttc     480
tgctggaatg atttcggtga gtagaagaat actactttct tcttaaaacc ctagtgttaa     540
atttccttta tttgattcca aaatttgtta ttgtgaaaca ggcaatcgat aggcttccat     600
tggttcctgg tgttcttgaa cttgtaggca tcggttacac aggagtgagt tcttcttct      660
ctttgtatca cttgaaccaa agctctcatg aacctgtttt gaggatatag atgattcatc     720
acttcacttt tggattaggg attagttctc tgaatttaga atccgaacat ctgcaattca     780
tatgagagata tgatatcaga aattgattgc tgcttcctcgc tagtgtttca atcttaaaag    840
acgtgtgtag tttgtttcaa ttgtgtgatg gaccttatta acatttggtt tttctatggc     900
agtggttcac ttcaagaac ctggtcttca accagacag gttaaccaat tctctcttta      960
actctgtgtt tggttgcatg taatactgag aatggaagac tcaaattctc gaggaaattg    1020
```

```
tttgttatct gtttcaggga ggctttgttt gagaaggtca agagcacata caaagacata    1080
ttagggagca gctgaatcaa aggaggaaga agaagaagaa gagcctttt gaggccattc      1140 atgaattgga atgaaggata tcaaaagaat ctaacacaaa ggccacgtcc ttccttcaat     1200 cttccttct tgtaactaaa taattttcat cctttctctc tctctgtctc tggtcttttt      1260
tagctcaaag tatcatccat ttatgtcaaa gtgttgtaaa ttcctcaaga ctatatatga     1320
gatgttttgt ttcattttcc aaaatttcaa actttgtccc catttagtct tctacccttc     1380
atgcatggtt agcttagctt aatgctgaac tgttgaataa cgatatgggc cttatgctaa     1440
aagaacaaaa ccttatgggt ctaaaaaaaa taagcccaat ataaaactat ggcccaaata     1500
agtttaggtc cattagagtg tgagaatagc gcgtgtagtg aaccgcacga gaatgcgcgt    1560
tcgattgttg gtgaagtagt cgtctagatt cccgggtcca ctgatgtttc tagtgtatca    1620
gacacgtgtc gacaaactgg tgggagagat taacgatctt aagtaggtcc cactagatca    1680
agatattata acgaattgac cttttaacc tttcaggtag tcccggaact cgtggcctag      1740
aatacaaaga aggttgtgaa caagttgatg ttaagatgga caagaatgta acttgaacaa    1800
aagctgaatc atctcttcag ccactagtat gttgacatat ggcagtttct tttgtagcct     1860
cgaaataaat aaattaaaaa gtttgaggtt aaagataatt atagtggctg agatttctcc    1920
atttccgtag cttctggtct cttttctttg tttcattgat caaagcaaa tcacttcttc       1980 ttcttcttct tctcgatttc ttactgtttt cttatccaac gaaatctgga attaaaaatg     2040 gaatcttat cgaatccaag ctgatttgt ttctttcatt gaatcatctc tctaaaggta       2100
cttaagattg atttattgtc atggtctttc ttattgtttg atgaataact tgacttgatt    2160 gtttttgtt ttgtggatta gtggaatttt gtaaagagaa gatctgaagt tgtgtagagg     2220
agcttagtga tggagacaaa ttcgtctgga gaagatctgg ttattaaggt aaattaacta    2280 aatttagg ggaagatgat tgttttaggt gtcaaagatt gagaatttta atgaaacttg      2340
atatagactc ggaagccata tacgataaca agcaacgtg aaaggtggac tgaggaagaa     2400
cataatagat tcattgaagc tttgaggctt tatggtagag catggcagaa gattgaaggt    2460 tgattttat ttcccttat atgtcttatt ttttgtgttt gcagaggttt gtcttcaaac      2520
tgatttgctt ttttcattt ggacagaaca tgtagcaaca aaaactgctg tccagataag    2580
aagtcacgct cagaaatttt tctccaaggt aaaatcggtt aattttgaaa tgatgttctc    2640
atcttcattg gcttaatgct taagacttat tgaaagccag gcaagttttc tgcttctttt    2700
gcttcttagt caggagatag atagattacg ttttagagt ttagtaatga gcaataagtc    2760
ttaaaatagt tggagaaatg acgagatgta atcgttttct tttgtttatg cctatatctt    2820
gttaatccac aaacatgtac atagattctt cagaagaatg ttagtttctt tagattcttc    2880
agataaactt gtgtcttctt accgattctg aggtagtggc aaaagtgggc tgagtgctag    2940
aaatttttga atgttccttg tgataagcca tagaggtaaa ccattttga ttttccagtt     3000 ctgtcattta aacttgttag gtgtcattag attttgttt gtttacgttt gtttagaggg    3060
taacaaaact actctcatct ctctcaggta gagaaagagg ctgaagctaa aggtgtagct    3120
atgggtcaag cgctagacat agctattcct cctccacggc ctaagcgtaa accaaacaat    3180
ccttatcctc gaaagacggg aagtggaacg atccttatgt caaaaacggg tgtgaatgat    3240
ggaaaagagt cccttggatc agaaaaagtg tcgcatcctg aggtgatttt catggtcata    3300
tggcatcttt ttgcagtgtg tcacattgct cctcatgtta ttaatacaga ttgtgtgctt    3360
cgtttataga tggccaatga agatcgacaa caatcaaagc ctgaagagaa aactctgcag    3420
```

```
gaagacaact gttcagattg tttcactcat cagtatctct ctgctgcatc ctccatgaat    3480
aaaagttgta tagagacatc aaacgcaagc actttccgcg agttcttgcc ttcacgggaa    3540
gaggtaaaaa acaatctttc attgctattt gaggttttaa gacgattagt acttttcatg    3600
aaactaaaac cgtgggggaa taacagggaa gtcagaataa cagggtaaga aaggagtcaa    3660
actcagattt gaatgcaaaa tctctggaaa acggtaatga gcaaggacct cagacttatc    3720
cgatgcatat ccctgtgcta gtgccattgg ggagctcaat aacaagttct ctatcacatc    3780
ctccttcaga gccagatagt catccccaca cagttgcagg agattatcag tcgtttccta    3840
atcatataat gtcaacccctt ttacaaacac cggctcttta tactgccgca actttcgcct    3900
catcattttg gcctcccgat tctagtggtg gctcacctgt tccagggaac tcacctccga    3960
atctggctgc catggccgca gccactgttg cagctgctag tgcttggtgg gctgccaatg    4020
gattattacc tttatgtgct cctcttagtt caggtggttt cactagtcat cctccatcta    4080
cttttggacc atcatgtgat gtagagtaca caaaagcaag cactttacaa catggttctg    4140
tgcagagccg agagcaagaa cactccgagg catcaaaggc tcgatcttca ctggactcag    4200
aggatgttga aaataagagt aaaccagttt gtcatgagca gccttctgca cacctgaga    4260 gtgatgcaaa gggttcagat ggagcaggag acagaaaaca gttgaccgg tcctcgtgtg     4320 gctcaaacac tccgtcgagt agtgatgatg ttgaggcgga tgcatcagaa aggcaagagg    4380
atggcaccaa tggtgaggtg aaagaaacga atgaagacac taataaaccct caaacttcag    4440 agtccaatgc acgccgcagt agaatcagct ccaatataac cgatccatgg aagtctgtgt    4500
ctgacgaggt acttacttgg actaaagatc aacttccttt atttcaaatc attttctcat    4560
ataaatattg tacattcggg tcgaattgcc ttccaagctc tcttctccag agaggtattg    4620
ccgcaaagtt ttacatatcg agaagaacac agagaggaag aacaacaaca acaagaacaa    4680
agatatccaa tggcacttga tcttaacttc acagctcagt taacaccagt tgatgatcaa    4740
gaggagaaga gaaacacagg atttcttgga atcggattag atgcttcaaa gctaatgagt    4800
agaggaagaa caggttttaa accatacaaa agatgttcca tggaagccaa agaaagtaga    4860
atcctcaaca acaatcctat cattcatgtg gaacagaaag atcccaaacg gatgcggttg    4920
gaaactcaag cttccacatg agactctatt ttcatctgat ctgttgtttg tactctgttt    4980
ttaagttttc aagaccactg ctacatttc ttttctttt gaggcctttg tatttgtttc    5040
cttgtccata gtcttcctgt aacatttgac tctgtattat tcaacaaatc ataaactgtt    5100
taatcttttt ttttccaacc tggaaagaac ttcactcaag gggctcttgt tcttgatata    5160
tgcaaacgac agagttccaa aacgtaatct tagcccatcc atcacccta agttgtctca    5220 taactcataa gtaagcacaa aa    5242
```

<210> SEQ ID NO 6
<211> LENGTH: 107
<212> TYPE: DNA
<213> ORGANISM: Arabidopsis thaliana

<400> SEQUENCE: 6

```
gcatcctgag gtgattttca tggtcatatg gcatctttt gcagtgtgtc acattgctcc      60
tcatgttatt aatacagatt gtgtgcttcg tttatagatg gccaatg                 107
```

<210> SEQ ID NO 7
<211> LENGTH: 24
<212> TYPE: DNA
<213> ORGANISM: Bemisia tabaci

```
<220> FEATURE:
<221> NAME/KEY: misc_feature
<222> LOCATION: (1)..(1)
<223> OTHER INFORMATION: n = inosine
<220> FEATURE:
<221> NAME/KEY: misc_feature
<222> LOCATION: (7)..(7)
<223> OTHER INFORMATION: n = inosine
<220> FEATURE:
<221> NAME/KEY: misc_feature
<222> LOCATION: (16)..(16)
<223> OTHER INFORMATION: n = inosine
<220> FEATURE:
<221> NAME/KEY: misc_feature
<222> LOCATION: (19)..(19)
<223> OTHER INFORMATION: n = inosine

<400> SEQUENCE: 7
ngcrtgnccr tgyttnccng tytt                                            24

<210> SEQ ID NO 8
<211> LENGTH: 21
<212> TYPE: DNA
<213> ORGANISM: Bemisia tabaci
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (12)..(12)
<223> OTHER INFORMATION: n = inosine
<220> FEATURE:
<221> NAME/KEY: misc_feature
<222> LOCATION: (18)..(18)
<223> OTHER INFORMATION: n = inosine

<400> SEQUENCE: 8
ggnaarcayg gncaygcnaa r                                               21

<210> SEQ ID NO 9
<211> LENGTH: 32
<212> TYPE: DNA
<213> ORGANISM: Bemisia tabaci

<400> SEQUENCE: 9
ccgggctcga ggccaaatcc tggccaactt tg                                   32

<210> SEQ ID NO 10
<211> LENGTH: 34
<212> TYPE: DNA
<213> ORGANISM: Bemisia tabaci

<400> SEQUENCE: 10
ccgggatcga ttttgtttgt tcgttgtca gctg                                  34

<210> SEQ ID NO 11
<211> LENGTH: 34
<212> TYPE: DNA
<213> ORGANISM: Bemisia tabaci

<400> SEQUENCE: 11
ccgggctgca gtttgtttgt tcgttgtca gctg                                  34

<210> SEQ ID NO 12
<211> LENGTH: 32
<212> TYPE: DNA
<213> ORGANISM: Bemisia tabaci

<400> SEQUENCE: 12
```

```
ccgggtctag agccaaatcc tggccaactt tg                              32

<210> SEQ ID NO 13
<211> LENGTH: 33
<212> TYPE: DNA
<213> ORGANISM: Arabidopsis thaliana

<400> SEQUENCE: 13
ccgggaagct tgcatcctga ggtgattttc atg                             33

<210> SEQ ID NO 14
<211> LENGTH: 33
<212> TYPE: DNA
<213> ORGANISM: Arabidopsis thaliana

<400> SEQUENCE: 14
ccgggctgca gcattggcca tctataaacg aag                             33

<210> SEQ ID NO 15
<211> LENGTH: 34
<212> TYPE: DNA
<213> ORGANISM: Meloidogyne javanica

<400> SEQUENCE: 15
ccgggctcga gtgttgtact tgccatcaag gacc                            34

<210> SEQ ID NO 16
<211> LENGTH: 35
<212> TYPE: DNA
<213> ORGANISM: Meloidogyne javanica

<400> SEQUENCE: 16
ccgggaagct tatatccggg aggagtacgc ggttc                           35

<210> SEQ ID NO 17
<211> LENGTH: 35
<212> TYPE: DNA
<213> ORGANISM: Meloidogyne javanica

<400> SEQUENCE: 17
ccgggctgca gatatccggg aggagtacgc ggttc                           35

<210> SEQ ID NO 18
<211> LENGTH: 34
<212> TYPE: DNA
<213> ORGANISM: Meloidogyne javanica

<400> SEQUENCE: 18
ccgggtctag atgttgtact tgccatcaag gacc                            34

<210> SEQ ID NO 19
<211> LENGTH: 24
<212> TYPE: DNA
<213> ORGANISM: Meloidogyne javanica

<400> SEQUENCE: 19
gttatgtaca gtctttccaa agcc                                       24

<210> SEQ ID NO 20
<211> LENGTH: 23
<212> TYPE: DNA
<213> ORGANISM: Meloidogyne javanica

<400> SEQUENCE: 20
```

-continued

```
ggttattggc cacgtcgatt ctg                                    23
```

<210> SEQ ID NO 21
<211> LENGTH: 23
<212> TYPE: DNA
<213> ORGANISM: Meloidogyne javanica

<400> SEQUENCE: 21

```
gtacttgatg aagtcacgaa gtc                                    23
```

<210> SEQ ID NO 22
<211> LENGTH: 45
<212> TYPE: DNA
<213> ORGANISM: Meloidogyne javanica

<400> SEQUENCE: 22

```
ttaatacgac tcactatagg gagaccctgt tcaccaggaa ctccg             45
```

<210> SEQ ID NO 23
<211> LENGTH: 27
<212> TYPE: DNA
<213> ORGANISM: coelenterates

<400> SEQUENCE: 23

```
cccgacgtca tggccaacac ttgtcac                                27
```

<210> SEQ ID NO 24
<211> LENGTH: 45
<212> TYPE: DNA
<213> ORGANISM: coelenterates

<400> SEQUENCE: 24

```
taatacgact cactataggg agaccactcc tgttgacgag ggtgt             45
```

<210> SEQ ID NO 25
<211> LENGTH: 55
<212> TYPE: PRT
<213> ORGANISM: Bemisia tabaci

<400> SEQUENCE: 25

Met Ala Asp Val Glu Ala His Phe Glu Thr Gly Asp Ser Gly Ala Ser
1               5                   10                  15

Thr Thr Tyr Pro Met Gln Cys Ser Ala Leu Arg Lys Asn Gly Phe Val
            20                  25                  30

Met Leu Lys Ala Arg Pro Cys Lys Ile Val Asp Met Ser Thr Ser Lys
        35                  40                  45

Thr Gly Lys His Gly His Ala
    50                  55

<210> SEQ ID NO 26
<211> LENGTH: 55
<212> TYPE: PRT
<213> ORGANISM: Drosophila yakuda

<400> SEQUENCE: 26

Met Ala Asp Met Asp Asp His Phe Glu Thr Thr Asp Ser Gly Ala Ser
1               5                   10                  15

Ser Thr Tyr Pro Met Gln Cys Ser Ala Leu Arg Lys Asn Gly Phe Val
            20                  25                  30

```
Met Leu Lys Ser Arg Pro Cys Lys Ile Val Glu Met Ser Thr Ser Lys
        35                  40                  45

Thr Gly Lys His Gly His Ala
    50              55
```